(12) United States Patent
Balan et al.

(10) Patent No.: US 12,420,021 B2
(45) Date of Patent: *Sep. 23, 2025

(54) DEVICE FOR INTRAOCULAR INJECTION

(71) Applicant: NEW WORLD MEDICAL, INC., Rancho Cucamonga, CA (US)

(72) Inventors: Vijay R Balan, Torrance, CA (US); Nico J. Slabber, Eastvale, CA (US)

(73) Assignee: NEW WORLD MEDICAL, INC., Rancho Cucamonga, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/511,668

(22) Filed: Nov. 16, 2023

(65) Prior Publication Data

US 2024/0082500 A1   Mar. 14, 2024

Related U.S. Application Data

(63) Continuation of application No. 17/187,110, filed on Feb. 26, 2021, now Pat. No. 11,844,934, which is a
(Continued)

(51) Int. Cl.
*A61M 5/315* (2006.01)
*A61B 17/3211* (2006.01)
*A61M 5/31* (2006.01)

(52) U.S. Cl.
CPC ..... *A61M 5/31563* (2013.01); *A61B 17/3211* (2013.01); *A61M 5/31581* (2013.01);
(Continued)

(58) Field of Classification Search
CPC .......... A61M 5/31563; A61M 5/31585; A61M 2005/3114; A61M 2210/0612;
(Continued)

(56) References Cited

U.S. PATENT DOCUMENTS 3,797,488 A   3/1974 Hurschman et al.
5,176,645 A * 1/1993 Guerrero ............... A61M 5/204
                                              604/150
(Continued)

FOREIGN PATENT DOCUMENTS

CA      2751699 A1    8/2010
CN    201088780 Y     7/2008
(Continued)

OTHER PUBLICATIONS

Chinese Notification to Complete Formalities of Registration for 201980039823.6, dated Sep. 27, 2023, 7 pages including translation.
(Continued)

*Primary Examiner* — James D Ponton
(74) *Attorney, Agent, or Firm* — MASCHOFF BRENNAN

(57) ABSTRACT

Devices and methods for intraocular fluid injection are disclosed. A device can include a surgical instrument for an ophthalmic procedure. The surgical instrument can include a handle. A fluid compartment can be coupled to the handle and configured to hold a substance. A tool can be coupled to the distal end of the handle and have a lumen configured to convey the substance into an intraocular site of a patient. A piston can be in the handle and configured to reciprocate along the longitudinal axis of the handle to draw the substance from the fluid compartment and eject the substance through the lumen of the tool. A push button can be on the lateral side of the housing and configured to engage the piston via a sloped surface to actuate a forward stroke of the piston towards the distal end of the handle.

17 Claims, 22 Drawing Sheets

Related U.S. Application Data continuation of application No. 16/706,538, filed on Dec. 6, 2019, now Pat. No. 10,946,145, which is a continuation of application No. PCT/US2019/027358, filed on Apr. 12, 2019.

(60) Provisional application No. 62/656,818, filed on Apr. 12, 2018.

(52) U.S. Cl.
CPC . *A61M 5/31585* (2013.01); *A61M 2005/3114* (2013.01); *A61M 2210/0612* (2013.01)

(58) Field of Classification Search
CPC .......... A61M 5/31526; A61M 5/31595; A61M 5/16809; A61M 5/3158; A61B 17/3211; A61F 9/00736; A61F 9/0008
See application file for complete search history.

(56) References Cited

U.S. PATENT DOCUMENTS

| | | | | |
|---|---|---|---|---|
| 5,456,672 | A * | 10/1995 | Diederich | B05B 11/1014 433/80 |
| 2003/0105430 | A1* | 6/2003 | Lavi | A61M 5/2033 604/890.1 |
| 2006/0047250 | A1 | 3/2006 | Hickingbotham | |
| 2006/0084921 | A1* | 4/2006 | Darnell | A61M 5/1424 604/164.02 |
| 2009/0082727 | A1 | 3/2009 | Moeller | |
| 2009/0275969 | A1 | 11/2009 | Kitamura et al. | |
| 2010/0211007 | A1 | 8/2010 | Lesch, Jr. et al. | |
| 2010/0234790 | A1* | 9/2010 | Tu | A61M 27/002 604/8 |
| 2013/0253402 | A1* | 9/2013 | Badawi | A61F 9/007 604/8 |
| 2014/0291355 | A1* | 10/2014 | Fago | A61M 5/31511 222/386 |
| 2017/0181892 | A1* | 6/2017 | Kahook | A61F 9/0133 |
| 2017/0245984 | A1* | 8/2017 | Germann | A61M 5/31595 |
| 2018/0028358 | A1 | 2/2018 | Andino | |

FOREIGN PATENT DOCUMENTS

| | | |
|---|---|---|
| CN | 101912325 A | 12/2010 |
| CN | 105813669 A | 7/2016 |
| CN | 105832460 | 8/2016 |
| CN | 205581650 U | 9/2016 |
| CN | 107223042 A | 9/2017 |
| CN | 206473659 U | 9/2017 |
| CN | 107249522 A | 10/2017 |
| EP | 2033577 | 3/2009 |
| JP | H05192360 A | 8/1993 |
| JP | 2004500220 A | 1/2004 |
| JP | 2007501687 A | 2/2007 |
| JP | 2016220383 A | 12/2016 |
| KR | 101290512 | 7/2013 |
| WO | WO-0178631 A2 | 1/2004 |
| WO | WO-2004110501 A2 | 12/2004 |
| WO | WO-2006029556 | 3/2006 |
| WO | WO-2013063525 A1 | 5/2013 |
| WO | WO-2013151904 A1 | 10/2013 |
| WO | WO-2017112893 A1 | 6/2017 |

OTHER PUBLICATIONS

Chinese Office Action for 2019800398236, dated Mar. 30, 2023, 19 pages including translation.
Chinese Office Action for Application No. 201980039823.6, dated Aug. 29, 2022, 14 pages including translation.
Extended European Search Report for Application No. 23156044.2, dated May 24, 2023, 7 pages.
International Search Report and Written Opinion for International Application No. PCT/US2019/027358 dated Jul. 4, 2019.
Japanese Office Action for Application No. 2020-555392, dated Aug. 8, 2023, 4 pages including translation.
Japanese Office Action for Application No. 2020-555392, dated Jan. 27, 2023, 7 pages including translation.

* cited by examiner

DEVICE FOR INTRAOCULAR INJECTION

CROSS-REFERENCE TO RELATED APPLICATIONS

This application is a continuation of U.S. patent application Ser. No. 17/187,110, entitled, "DEVICE AND METHOD FOR INTRAOCULAR FLUID INJECTION," filed Feb. 26, 2021, issued as U.S. Pat. No. 11,844,934 on Dec. 19, 2023, which is a continuation of U.S. patent application Ser. No. 16/706,538, entitled, "DEVICE AND METHOD FOR INTRAOCULAR FLUID INJECTION," filed Dec. 6, 2019, issued as U.S. Pat. No. 10,946,145 on Mar. 16, 2021, which is a continuation of and claims priority to International Patent Application No. PCT/US2019/027358, entitled, "DEVICE AND METHOD FOR INTRAOCULAR FLUID INJECTION," filed Apr. 12, 2019, which claims the benefit of priority under 35 U.S.C. § 119 from U.S. Provisional Application No. 62/656,818, entitled "FLUID INJECTION FOR TRABECULECTOMY," filed Apr. 12, 2018, the entirety of which are incorporated herein by reference.

TECHNICAL FIELD

Disclosed embodiments relate in general to medical devices and procedures, and more particularly to a surgical instrument and method for intraocular fluid injection.

BACKGROUND OF THE DISCLOSURE

Glaucoma refers to a group of eye conditions that cause damage to an eye's optic nerve, typically due to increased intraocular pressure (pressure in the eye). Millions of people suffer from glaucoma with symptoms that include vision loss, or in extreme cases, irreversible blindness.

BRIEF DESCRIPTION OF THE DRAWINGS

The accompanying drawings, which are included to provide further understanding of the subject technology and are incorporated in and constitute a part of this description, illustrate aspects of the subject technology and, together with the specification, serve to explain principles of the subject technology.

FIG. 1A is a side view of the medical instrument with a coupled fluid source. FIG. 1B is an isometric view of the medical instrument with the fluid source removed and a fluid connector interface exposed. FIG. 1C is a side view of the medical instrument with a cap covering the fluid connector.

FIG. 2A depicts a mode of operation in which a user actuates a button of the medical instrument using a thumb. FIG. 2B depicts a mode of operation in which a user actuates a button of the medical instrument using an index finger.

FIG. 4A illustrates the fluid transfer mechanism with the button in an upwards and non-actuated position. FIG. 4B illustrates the fluid transfer mechanism with the button in a depressed and actuated position.

FIG. 5A is a side view showing the pre-fill component coupled to a handle of the medical instrument. FIG. 5B is a longitudinal cross-section view showing the pre-fill component coupled to the handle. FIG. 5C is a side view of the pre-fill component at a first stage of operation. FIG. 5D is a side view of the pre-fill component at a second stage of operation. FIG. 5E is a side view of a sealing member and an interface member of the pre-fill component. FIG. 5F is a longitudinal cross-section view of the sealing member of the pre-fill component. FIG. 5G is a side view of the interface member of the pre-fill component.

DETAILED DESCRIPTION

Figure 1A:
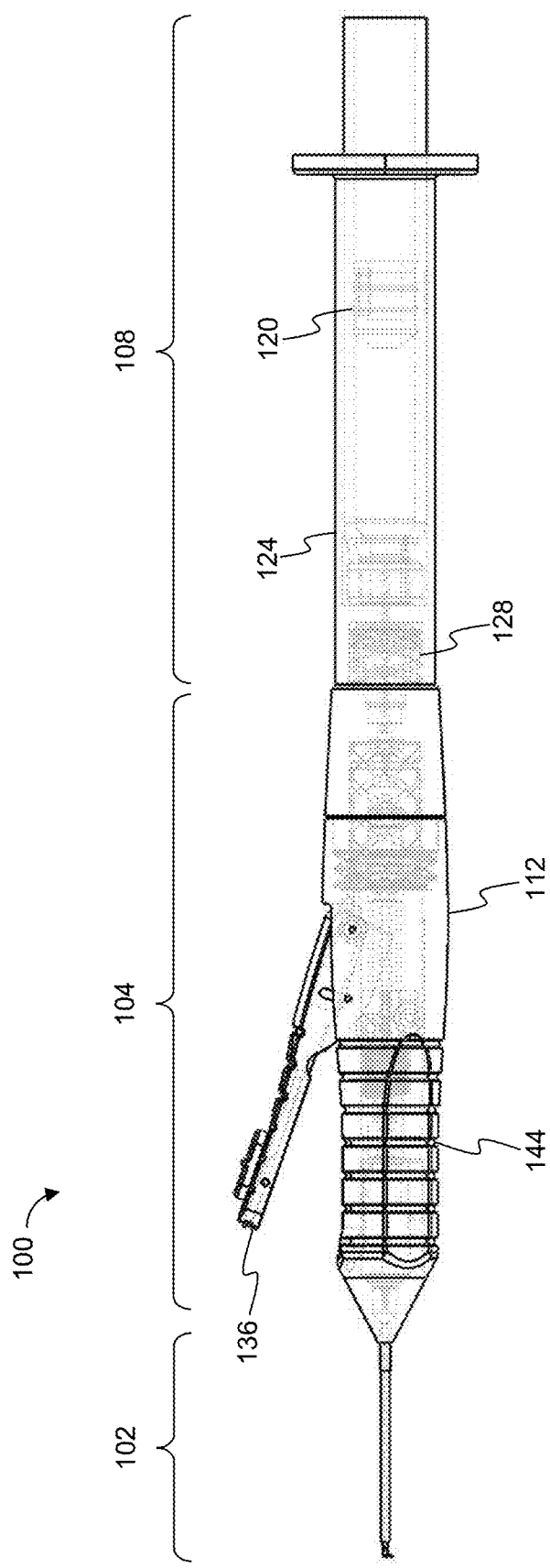
FIGS. 1A-1C illustrate various views of an example of a medical instrument, in accordance with some embodiments.

The detailed description set forth below is intended as a description of various implementations and is not intended to represent the only implementations in which the subject technology may be practiced. As those skilled in the art would realize, the described implementations may be modified in various different ways, all without departing from the scope of the present disclosure. Accordingly, the drawings and description are to be regarded as illustrative in nature and not restrictive.

Embodiments disclosed herein may be implemented as instruments or devices suitable for ophthalmic procedures, including, for example, devices having blades or other tools configured to cut or remove portions of tissue from a trabecular meshwork or other intraocular tissue. Some examples of such devices are disclosed in U.S. Non-Provisional application Ser. No. 15/791,204, filed on Oct. 23, 2017, and U.S. Non-Provisional application Ser. No. 15/389,328, filed on Dec. 22, 2016, the entirety of each of which is incorporated herein by reference. Embodiments disclosed herein may be implemented as devices having microcannulas or orifices configured to inject a substance into Schlemm's canal or other intraocular sites. Some examples of such devices are disclosed in U.S. Provisional Application No. 62/750,151, filed on Oct. 28, 2018, and U.S. Non-Provisional application Ser. No. 15/847,770, filed on Dec. 19, 2017, the entirety of each of which is incorporated herein by reference.

To facilitate the understanding of the present disclosure, a number of terms are defined below.

Terms defined herein have meanings as commonly understood by a person of ordinary skill in the areas relevant to the present disclosure. Terms such as "a," "an," and "the" are not intended to refer to only a singular entity, but include the general class of which a specific example may be used for illustration.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

The term "therapeutically effective amounts" or "pharmaceutically effective amounts", as used herein means that amount which, when administered to a subject or patient for treating a disease, is sufficient to effect such treatment for the disease or to ameliorate one or more symptoms of a disease or condition (e.g. ameliorate pain).

As used herein, the terms "treat" and "treating" are not limited to the case where the subject (e.g. patient) is cured and the disease is eradicated. Rather, embodiments of the present disclosure also contemplate treatment that merely reduces symptoms, improves (to some degree) and/or delays disease progression. It is not intended that embodiments of the present disclosure be limited to instances wherein a disease or affliction is cured. It is sufficient that symptoms are reduced.

As used herein "goniotomy" refers to a surgical procedure primarily used to treat various types of glaucoma (e.g., primary open angle glaucoma).

As used herein "trabecular meshwork" refers to area of tissue in the eye located around the base of the cornea, near the ciliary body, (between the scleral spur and Schwalbe's line) and is responsible for draining the aqueous humor from the eye via the anterior chamber (the chamber on the front of the eye covered by the cornea). The tissue is spongy and lined by trabeculocytes; it allows fluid to drain into a circular channel in the eye called Schlemm's canal and eventually flowing into the blood system.

As used herein "Schlemm's canal" refers to a circular channel in the eye that collects aqueous humor from the anterior chamber and delivers it into the bloodstream via the collector channels and anterior ciliary veins.

As used herein "eye diseases" refers to various conditions of the eye including, but not limited to Glaucoma—optic neuropathy, Glaucoma suspect—ocular hypertension, Primary open-angle glaucoma, Primary angle-closure glaucoma, primary open angle glaucoma, normal or low tension glaucoma, pseudoexfoliation glaucoma, pigment dispersion glaucoma, angle closure glaucoma (acute, subacute, chronic), neovascular or inflammatory glaucoma, ocular hypertension, and other types of glaucoma that are related to dysregulation of intraocular pressure.

As used herein "hypotony" refers to reduced intraocular pressure. The statistical definition of hypotony is intraocular pressure ("TOP") less than 6.5 mmHg, which is more than 3 standard deviations below the mean IOP. The clinical definition of hypotony is IOP low enough to result in pathology (vision loss). The vision loss from low IOP may be caused by corneal edema, astigmatism, cystoid macular edema, maculopathy, or other condition. Hypotony maculopathy is characterized by a low IOP associated with fundus abnormalities, including chorioretinal folds, optic nerve head edema in the acute setting, and vascular tortuosity.

As used herein "Schwalbe's line" refers to the anatomical line found on the interior surface of the eye's cornea, and delineates the outer limit of the corneal endothelium layer. Specifically, it represents the termination of Descemet's membrane.

As used herein "Descemet's membrane" refers to the basement membrane that lies between the corneal proper substance, also called stroma, and the endothelial layer of the cornea.

As used herein "scleral spur" refers to an annular structure composed of collagen in the human eye, a protrusion of the sclera into the anterior chamber. It is the origin of the longitudinal fibers of the ciliary muscle and is attached anteriorly to the trabecular meshwork. Open-angle glaucoma (OAG) and closed-angle glaucoma (CAG) may be treated by muscarinic receptor agonists (e.g., pilocarpine), which cause rapid miosis and contraction of the ciliary muscles, this pulls the scleral spur and results in the trabecular meshwork being stretched and separated. This opens the fluid pathways and facilitates drainage of the aqueous humour into the canal of Schlemm and ultimately decreasing intraocular pressure.

As used herein "Trabectome®" refers to a minimally invasive glaucoma surgical electrosurgical or ablation tool for the surgical management of adult, juvenile and infantile glaucoma. Unlike a trabeculectomy, the surgery with a Trabectome® should not create an external filtering bleb or require leaving a permanent hole in the eye. Instead, the Trabectome® electro-surgical handpiece opens access to the eyes natural drainage system.

Minimally invasive surgical procedures involving ocular incisions and/or intraocular fluid injection can be useful for treating glaucoma and other eye conditions. For example, in a Trabeculectomy, a surgeon can use an ophthalmic blade inserted through an incision in the eye to remove a portion of the trabecular meshwork, thereby improving outflow of the aqueous humour (AH) and relieving intraocular pressure contributing to glaucoma.

During the removal of the trabecular meshwork using an ophthalmic blade, some cases have been observed in which minor bleeding occurs. When bleeding occurs during the surgery, the blood can cover up the trabecular meshwork and Schlemm's canal, creating a visual obstruct. One method of dealing with the blood reflux involves removing the ophthalmic blade from the eye and inserting a viscoelastic syringe. The viscoelastic syringe can be used to push the blood reflux back into the Schlemm's canal and collecting channels or move the blood away from the trabecular meshwork. Once the blood is pushed away from the trabecular meshwork, the viscoelastic syringe is removed from the eye and ophthalmic blade is re-inserted to continue the surgery.

Embodiments disclosed herein include medical instruments and related methods that may be used in an ophthalmological procedure without a need for inserting and removing a separate viscoelastic syringe when such bleeding occurs. The disclosed embodiments include, among other things, a surgical instrument having an ophthalmic blade and integrated fluid delivery mechanism for intraocular injection of a viscoelastic fluid. It will be appreciated that various embodiments and principles disclosed herein may additionally or alternatively be employed for other purposes or for other medical or surgical procedures.

Figure 1B:
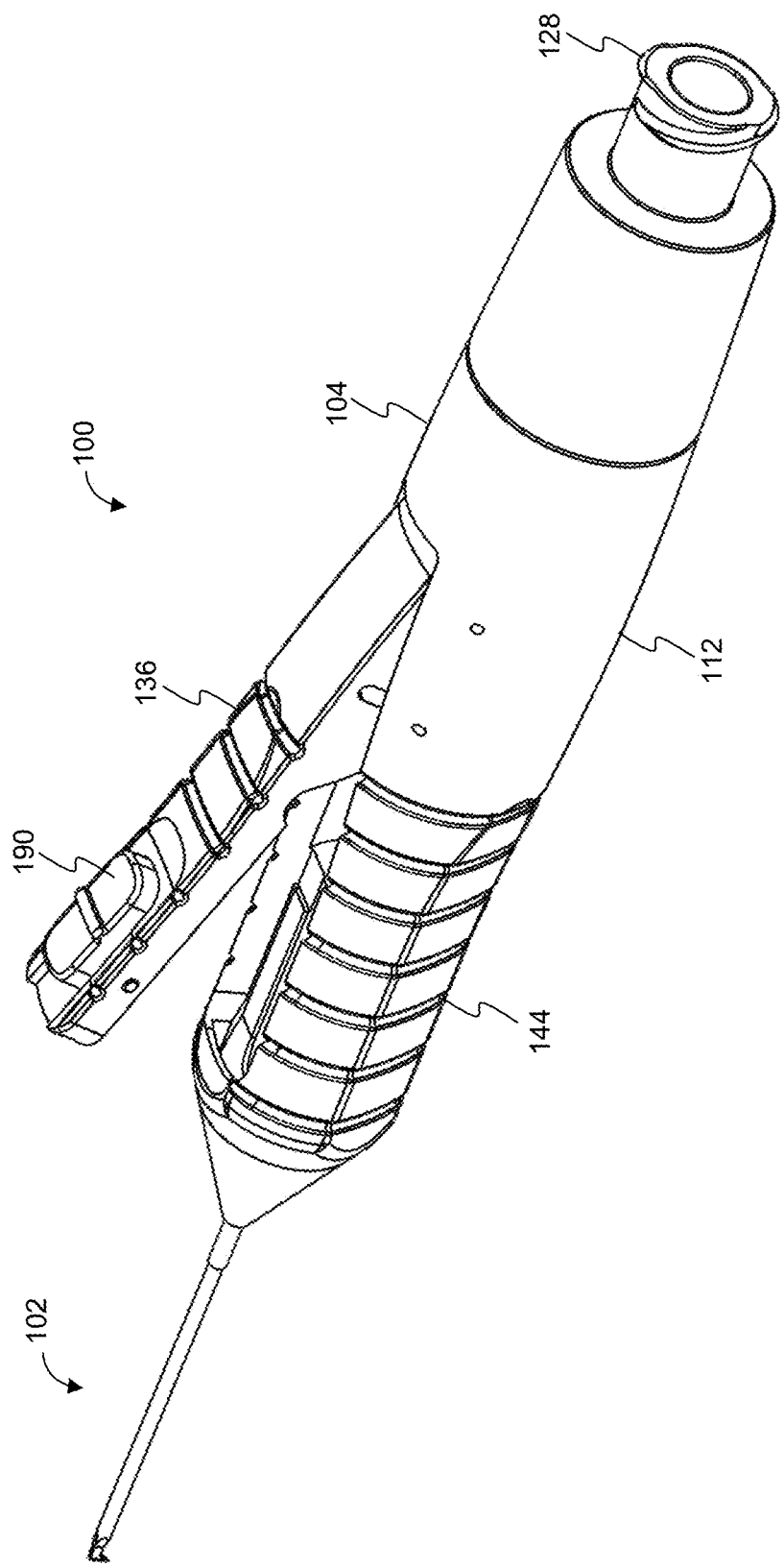
Figure 1C:
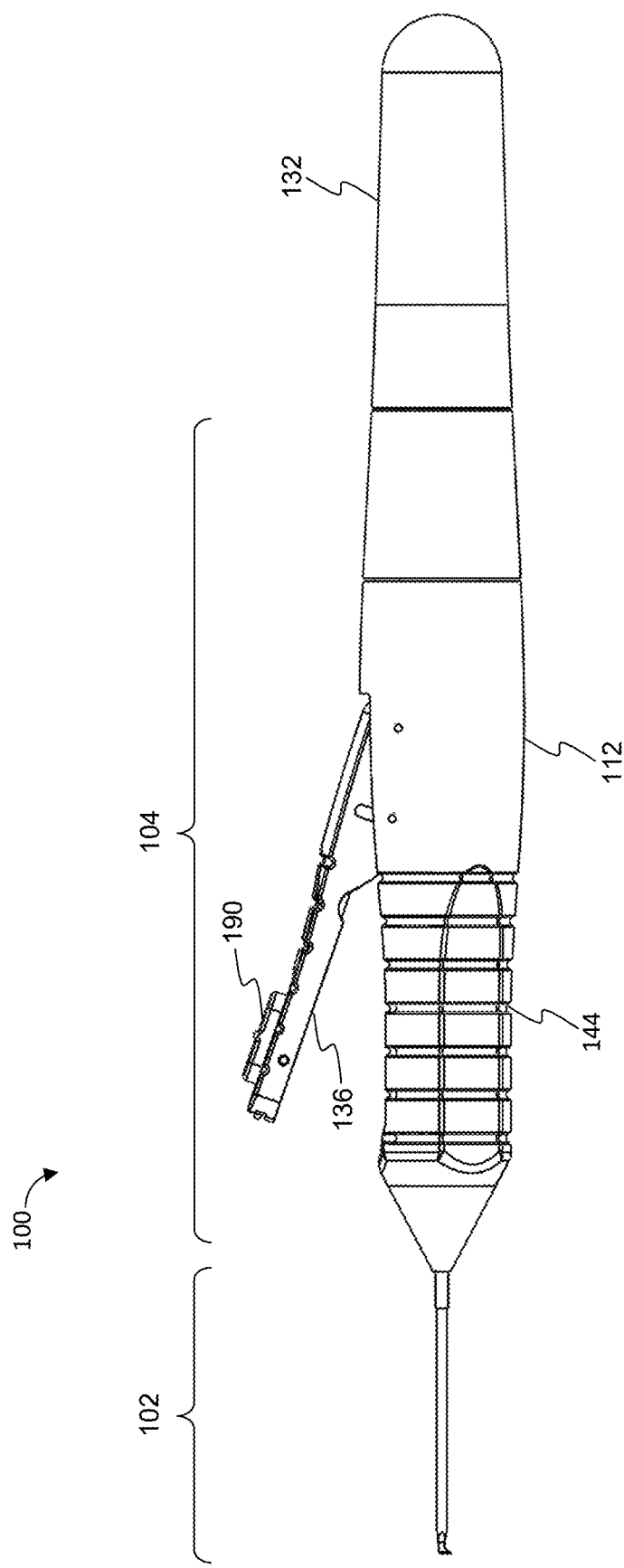

Turning now to the figures, FIGS. 1A-1C illustrate various views of an example medical instrument 100 that may employ principles of this disclosure. FIG. 1A is a side view of the instrument 100 in a configuration with a removable syringe attached. FIG. 1B is an isometric view of the instrument 100 in a configuration without the removable syringe and with a connector exposed. FIG. 1C is a side view of the instrument 100 in a configuration with a removable cap attached.

Referring to FIGS. 1A-1C, the instrument 100 generally includes a tool section 102 and a handle 104. The handle 104 is configured to interface with a fluid source 108, and the instrument 100 is generally configured to deliver fluid to a target site. In particular, the instrument 100 may be configured to deliver fluid from the fluid source 108, through the handle 104, and through the tool section 102 to a target site of the patient upon actuating a fluid transfer mechanism in the handle 104. Additionally or alternatively, the instrument 100 may be configured to transfer fluid through a channel in the handle 104 upon depressing a plunger 120 (e.g., via force applied by a finger to the proximal end of the plunger) or otherwise ejecting fluid from the fluid source 108.

The handle 104 includes a housing 112 having a connector or interface for coupling to the fluid source 108. More particularly, the housing 112 includes a luer lock connector 128 configured to removably attach to a component of the fluid source 108, such as a syringe 124 and/or a pre-fill component 300 (FIGS. 5A-5G) that contains a fluid compartment (e.g., a barrel) for holding a desired liquid or substance. As appropriate, the syringe 124 may be attached or removed from the housing 112 via the luer lock connector 128 through rotational or twisting motion between the housing 112 and the syringe 124. In some embodiments, the syringe 124 is implemented as a viscoelastic syringe for holding a viscoelastic fluid or substance of a type useful for ophthalmic procedures. The instrument 100 may be designed to handle cohesive, dispersive, or both cohesive and dispersive viscoelastic materials. Additionally or alternatively, the instrument 100 may be compatible with other fluids (e.g., saline, medicinal liquids, etc.) suitable for a variety of ocular or other medical procedures.

As shown in FIG. 1C, the instrument may be further provided with a removable cap 132 that attaches to the housing 112 via the luer lock connector 128, and which may, for example, serve to protect or isolate components of the instrument during transport or periods of non-use. It will be appreciated that while a luer lock connector 128 is shown, any of a variety of other standard or non-standard connectors may be included for fluidic coupling, as appropriate. Further, while a connector facilitating removable attachment of the fluid source 108 is shown, in some embodiments the handle 104 or the housing 112 may additionally or alternatively be provided with an integral fluid compartment for holding a desired fluid. More generally, in various embodiments the tool section 102, handle 104, and fluid source 108 may be removably attached, or any two or more of these components may be integrally formed or provided as a single unit.

Figure 2A:
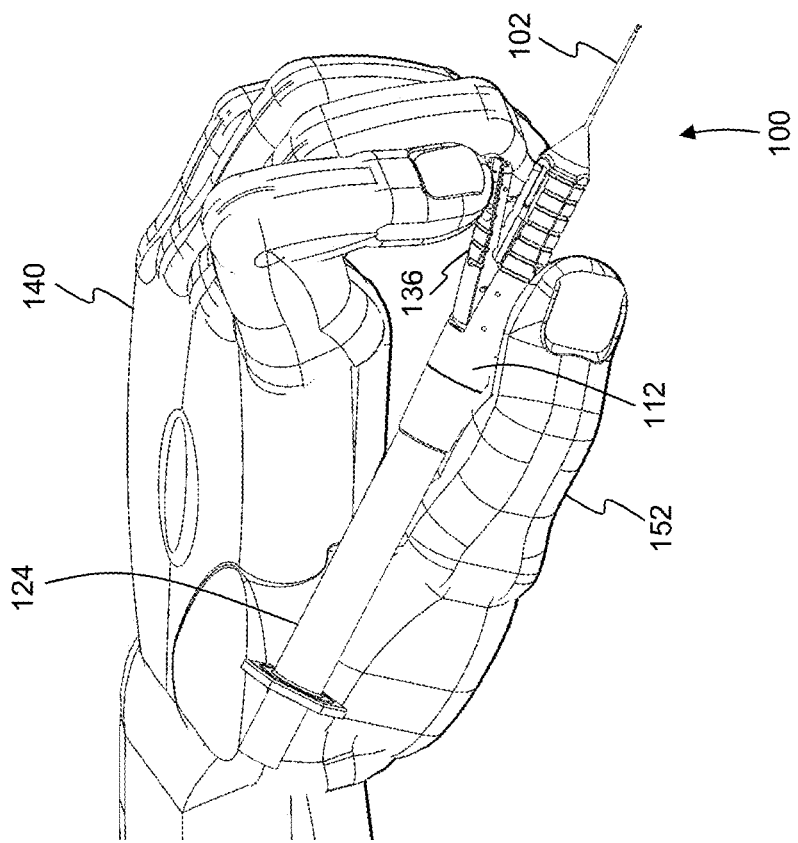
FIGS. 2A-2B illustrates examples of modes of operating a medical instrument.
Figure 2B:
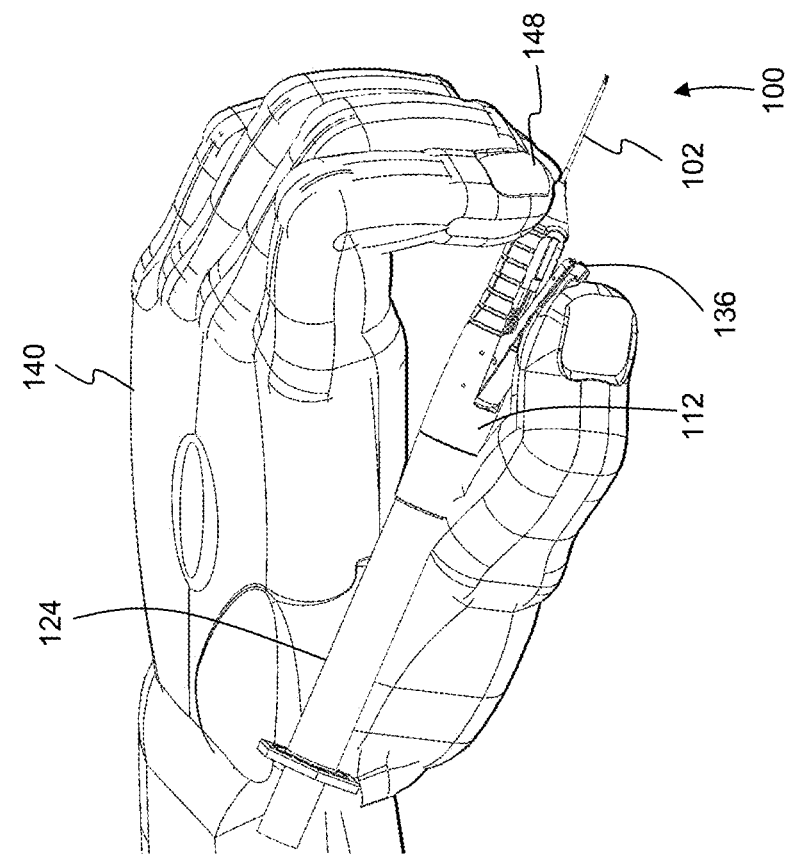

FIGS. 2A-2B are illustrations showing example modes of operating the instrument 100.

As shown in FIGS. 1A-2B, the handle 104 is equipped with a button 136 that may be used to actuate a fluid transfer mechanism. In particular, when pressed the button 136 may be configured to deliver a dosage of fluid from the syringe 124 through actuation of a fluid transfer mechanism employed in the handle 104. The housing 112 may have a shape that permits gripping of the instrument by a human hand 140 or otherwise permits manipulation of the surgical instrument by an operator. For example, as illustrated the housing 112 may be configured as an elongate tubular or cylindrical member that permits grasping of the instrument, which facilitates precise control over incisions made with the tool section 102 or accurate insertion of the tool section 102 into a fluid injection site of a patient. An exterior surface or lateral side of the housing 112 further includes grip-enhancing features 144, including a contoured profile and a series of ring indentations.

As shown in FIGS. 2A-2B, the button 136 is disposed on a lateral side of the handle 104. In particular, the button 136 is disposed on a lateral side of the housing 112. This may facilitate pressing of the button 136 with ease or without a need for repositioning of the instrument 100 using a digit of the hand 140 while the instrument is manipulated using a grip that also facilitates precise control. For example, as shown in FIG. 2A the button 136 may be positioned in a user's hand 140 for actuation using a thumb 152. As another example, as shown in FIG. 2B the button 136 may be positioned in a user's hand 140 for actuation using an index finger 148.

Figure 3:
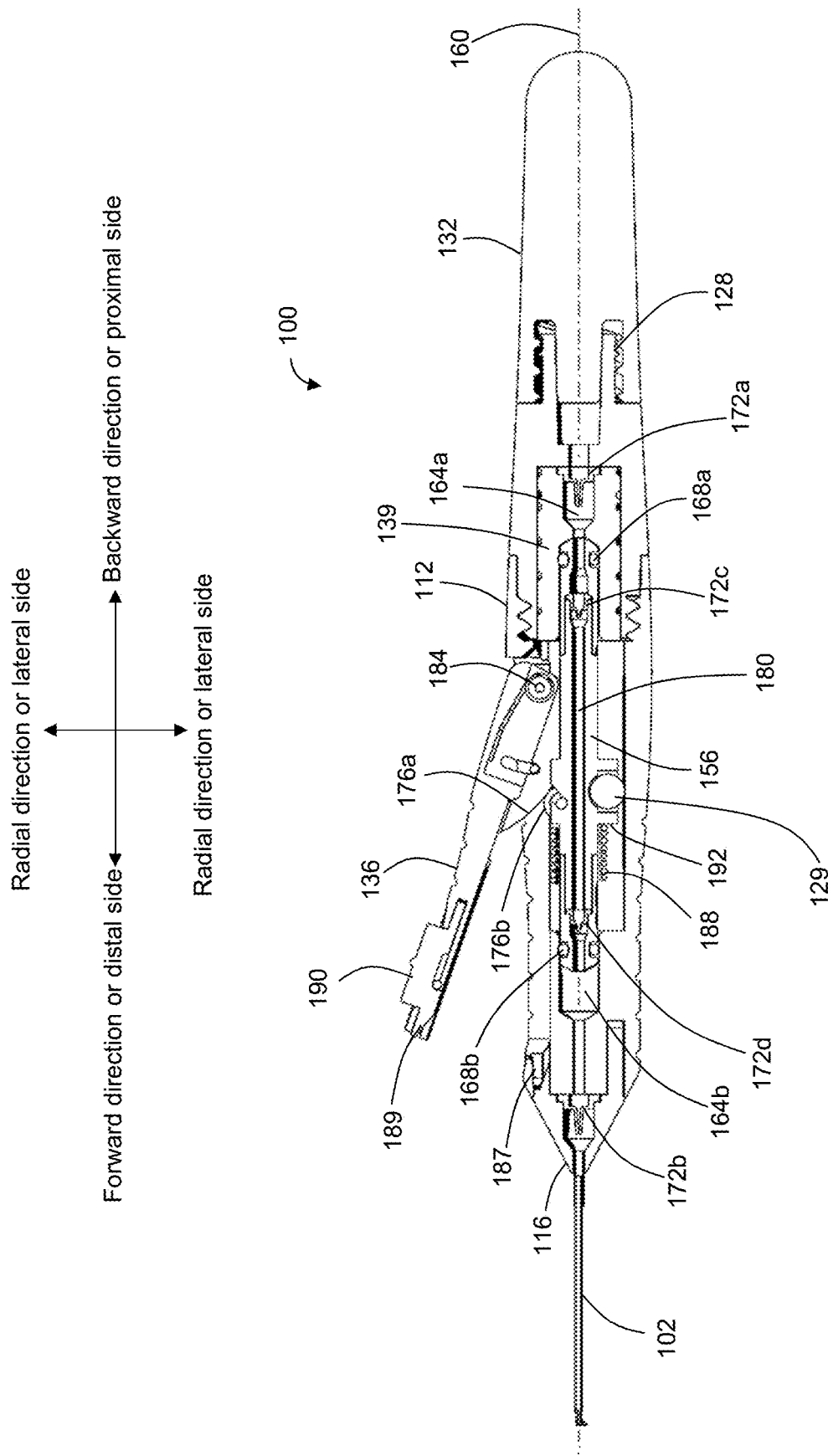
FIG. 3 illustrates a longitudinal cross-section view of a medical instrument showing an example of a fluid transfer mechanism.

FIG. 3 is a side view cross section of the instrument 100 illustrating components of a fluid transfer mechanism in detail. FIG. 3 shows the handle 104 of the instrument 100 with a removable cap 132 attached and with the tool section 102 attached. In FIG. 3, the housing 112 is shown as being composed of several pieces rigidly fixed together, but in other embodiments, the housing 112 may be composed of one integral piece. The housing 112 may be made from any of a variety of suitable materials, such as plastics, metals, and the like.

As shown in FIG. 3, the fluid transfer mechanism includes a piston 156 disposed in an interior of the housing 112. The piston 156 is generally configured to move relative to the housing 112, and more particularly, is configured to reciprocate within the housing for pumping or otherwise transferring fluid. As shown in FIG. 3, the housing 112 is configured as an elongate tubular housing defining a longitudinal axis 160 (e.g., cylindrical axis), and the piston 156 is configured to reciprocate back and forth within an interior cavity of the housing 112 along the longitudinal axis 160 an axial direction of the housing 112.

The interior cavity of the housing 112 includes one or more sealed chambers 164a,b that may be implemented as cylinders for compression and expansion by the piston 156. More particularly, the interior cavity of the housing 112 includes a pair of complementary chambers, including a fluid entry chamber 164a and a fluid exit chamber 164b disposed on opposing sides of the piston 156. The chambers are configured in a complementary fashion such that a compression stroke of the piston 156 for one of the chambers corresponds to an expansion stroke for the other chamber, and vice versa.

As illustrated, the entry chamber 164a may be sealed with an O-ring 168a disposed between a lateral exterior surface of the piston 156 and an interior surface of the cavity. The second chamber 164b may be sealed with an O-ring 168b disposed between a lateral exterior surface of the piston 156 and an interior surface of the cavity. More generally, in various embodiments either or both of the chambers 164a,b may be sealed using any of a variety of other appropriate seals or sealing elements.

The fluid transfer mechanism also generally includes a series of valves 172a-d and a fluidic channel 180 extending through the piston to facilitate compression, expansion, and transfer of the fluid within the mechanism as appropriate. As further described below, the fluid transfer mechanism may be designed to transfer fluid in a forward direction, from a proximal end to a distal end.

Referring to FIG. 3, an entry valve 172a is disposed at a fluid entry port of the entry chamber 164a. The fluid entry port may be disposed at the position of the luer lock connector 128. As shown in FIG. 3, the entry valve 172a may be fixedly attached to the housing 112 and disposed at a proximal end of the entry chamber 164a. Alternatively, the entry valve 172a may be provided as part of the syringe 124 or fluid source 108 (not shown in FIG. 3), or the fluid entry port may be disposed in another physical location relative to the entry chamber 164a. The entry valve 172a may be a check valve (or one-way valve) of a type that permits fluid flow across it in a direction into the entry chamber 164a but prevents fluid flow across it in a direction out of the entry chamber 164a.

An exit valve 172b is disposed at a fluid exit port of the exit chamber 164b, which corresponds to the position of the tool section 102 or a tool interface 116 configured to couple to a tool section 102. The tool interface 116 can be configured as a luer lock connector for coupling to a removable tool or provide a fixed fastening mechanism (e.g., welding, adhesives, screws, etc.) As shown in FIG. 3, the exit valve 172b may be fixedly attached to the housing 112 and disposed at a distal end of the exit chamber 164b. Alternatively, the exit valve 172b may be provided as part of the tool section 102=, or the fluid exit port may be disposed in another physical location relative to the exit chamber 164b. The exit valve 172b may be a check valve of a type that permits fluid flow across it in a direction out of the exit chamber 164b but prevents fluid flow across it in a direction into the exit chamber 164b.

One or more piston valves 172c,d are disposed on the piston 156 in a fluidic pathway extending through the piston 156. In particular, the piston 156 includes a channel 180 extending through it for transferring fluid from the entry chamber 164a to the exit chamber 164b, with one or more piston valves 172c,d disposed in the piston channel 180 or otherwise disposed in the fluidic pathway defined by the piston channel 180. Each of the piston valves 172c,d may be a check valve (or one-way valve) of a type that permits fluid flow across it in a forward direction, e.g., towards a distal side or in direction extending from the entry chamber 164a to exit chamber 164b, but prevents fluid flow across it in the opposite direction.

The piston channel 180 may optionally be segmented into a plurality of sub-channels, each terminating in a respective piston valve. For example, the piston channel 180 may include a first sub-channel terminating in a first piston valve that feeds fluid into a second sub-channel terminating in a second piston valve, and so forth. To facilitate manufacturing thereof, the piston 156 itself may be segmented into a plurality of components or pieces that are fixedly attached to one another, which may facilitate manufacturing of a piston having multiple piston channels. Alternatively, the piston 156 may be a unitary and integral construction.

A useful metric of a chamber may be a compression ratio (or its inverse, a expansion ratio) corresponding to a ratio of the internal volume of the chamber at is maximum and minimum points, which may correspond to a position of the piston at each end of its stroke. In various embodiments, the compression ratio or expansion ratio of a chamber may be determined by the location of the valves and diameter of the piston in the chamber. Segmenting the channel may be useful, for example, for increasing or tuning an effective compression and/or expansion ratio of one or more of the chambers for a given interior volume or piston stroke. For example, with reference to FIG. 3, the expansion ratio of the entry chamber 164a is made greater by the existence of the piston valve 172c between the piston valve 172d and entry valve 172a, relative to if this piston valve 172c were omitted. Since the internal volume of the sub-channel between piston valves 172c and 172d is essentially held constant during the expansion stroke of the piston 156, this internal volume is effectively removed from the equation. As a result, a greater expansion ratio in the entry chamber 164a, and thus, a greater suction force across the entry valve 172a, may be achieved for a given length of the stroke for the piston. It will be appreciated that while the example shows two piston valves and segmentation into two sub-channels, more or fewer sub-channels or piston valves may be utilized in various embodiments, as appropriate. Additionally or alternatively, adjusting the compression ratio can modify the volume of each dosage provided by the mechanism by changing a volume of fluid held in the exit chamber 164b that is ejected upon actuation of the piston 156.

According to some embodiments, a dose adjustment member 139 can be included in the handle 104. The dose adjustment member 139 can be, for example, a removable component or a movable component (e.g., slidable, twistable, etc.) that is configured to permit adjustment of the compression ratio. For example, the dose adjustment member 139 may be a removable component in the interior cavity of the housing 112 that can be swapped by a user or during manufacturing to tune the length of travel of the piston to adjust the compression ratio, and thereby the dosage delivered at each piston stroke or button press. As another example, the dose adjustment member 139 can be coupled to a user interface components, such as a slider or twist mechanism on the handle, that is configured to move the dose adjustment member 139 to various positions along the inner cavity of the housing 112 to constrain the travel of the piston to change the length of the piston stroke to two or more different user defined dosage volumes.

It will be appreciated that while a pair of complementary compression/expansion chambers 164a,b and corresponding valves 172a,b are shown, in various embodiments more or fewer chambers or valves may be included, as appropriate. For example, by eliminating one or the other of the entry chamber 164a or exit chamber 164b, the cost and complexity of the device may be reduced. Control of fluid flow may be greater with an increased number of chambers and valves.

Referring again to FIG. 3, the fluid transfer mechanism may further include or otherwise cooperate with a button 136. The button 136 is implemented as a mechanical button that is coupled to the piston 156 and configured to generate axial motion of the piston 156. In particular, the button 136 includes an engagement member 176a coupled to a corresponding engagement member 176b of the piston 156. The engagement members 176a, 176b can be, for example, sloped surfaces and/or wheels that are configured to engage each other to drive motion of the piston upon depression of the button 136. For example, the engagement member 176a of the button 136 can be a sloped surface, such as a ramp disposed on an interior surface of the button 136, while the engagement member 176b of the piston can be a complementary sloped surface, such as a ramp disposed on an exterior surface of the piston 156. Sliding engagement between the corresponding sloped surfaces may generate axial motion of the piston 156, as the button is depressed to convert depression of the button to distal motion of the piston. As another example, one of the button or the piston can include a sloped surface and the other of the button or the piston can include a wheel to facilitate engagement by rolling contact between the button and the piston that drives the motion of the piston upon depression of the button. Such a rolling engagement mechanism may reduce friction to facilitate smoother operation and actuation by the user. In the example shown in FIG. 3, the engagement member 176*a* of the button 136 includes a sloped surface, and the engagement member 176*b* of the piston includes a wheel. However, it is contemplated that these engagement members can be switched so that the button includes a wheel and the piston includes a sloped surface, for example. In the example shown, the button 136 is also pivotally attached to the housing 112 via a hinge 184, which may permit sliding or rolling engagement between the corresponding engagement members as the button 136 pivots about the hinge 184.

The piston 156 is biased to a position at an end of its stroke. This may also bias the button 136 to an upward or release position. In particular, a return spring 188 is included that biases the piston 156 towards the proximal end of the housing 112. The return spring 188 is implemented as a coil spring disposed around a shaft of the piston 156 and coupled between an axial surface of the housing and an axial surface 192 of the piston 156. To permit coupling in this fashion, the piston 156 includes a step disposed on its exterior surface, as shown in FIG. 3. It will be understood that while a return spring 188 is shown in a particular configuration, it will be appreciated the return spring may be modified or positioned differently, or any of a variety of biasing elements (e.g., magnets, torsion springs, etc.) may be used to bias the piston 156. As but one example, while the return spring 188 is shown as an axial coil spring abutting axial surfaces of the housing 112 and the piston 156, a similar effect may be achieved by implementing the return spring as a torsion spring in the hinge 184. In some embodiments, both an axial spring 188 and a torsion spring in the hinge 184 may be used, where the torsion spring returns the button to a non-actuated position more quickly than the axial spring 188 returns the piston to the proximal position, thereby providing for improved user experience. Biasing the button 136 and the piston 156 in this fashion may allow each button press to trigger a single stroke of the piston 156 and, accordingly, dispense a single dosage of fluid via the fluid transfer mechanism.

Figure 4B:
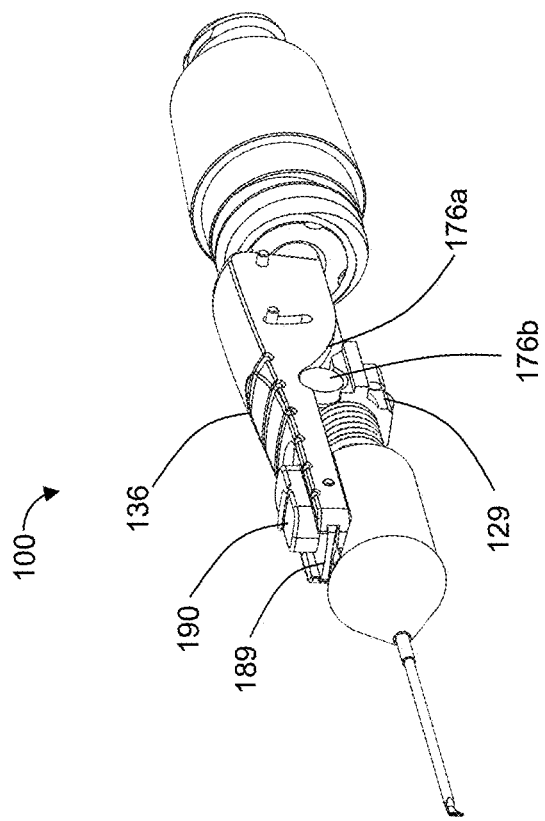
FIGS. 4A-4B illustrate isometric views of a medical instrument with portions of a housing removed to show a fluid transfer mechanism in various stages of operation.
Figure 4A:
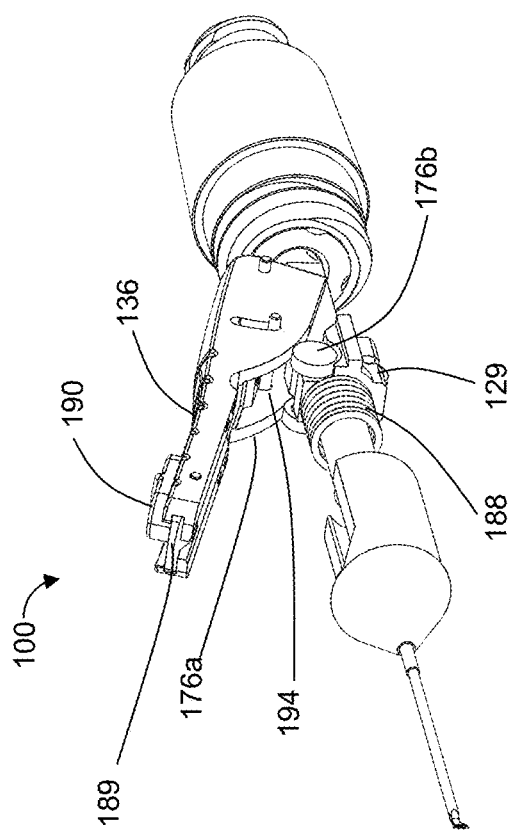

FIGS. 4A-4B show the instrument 100 in isometric view with portions of the housing 112 removed to allow for viewing of the fluid transfer mechanism in various stages of operation. In particular, FIG. 4A shows the mechanism with the piston 156 in a backwards and biased position and with the button 136 in an upwards and biased position. FIG. 4B shows the mechanism with the piston 156 in a forwards and actuated position and the button 136 in an actuated and depressed position. FIGS. 4A-4B also show in more detail an example of how engagement between the button 136 and the piston 156 can generate axial motion of the piston 156. As the button 136 is depressed and moved from the position in FIG. 4A to the position in FIG. 4B, the piston and button may roll or slide against each other to drive the piston forward. As shown in FIG. 4A, the button 136 may further include a groove 194 for accommodating a shaft 198 of the piston and facilitating good contact between the corresponding engagement members 176*a,b* by permitting the engagement members 176*a,b* to be positioned around the shaft 198. As shown in FIGS. 3-4B, the piston 156 may include one or more wheels 129 that couple the piston to the housing so that the piston can roll along the housing as it translates axially, thereby reducing friction during reciprocating motion of the piston. Additionally or alternatively, it is contemplated that such the wheel 129 can be positioned on an interior side of the housing 112.

It will also be appreciated that while a mechanical button is shown in various embodiments, the instrument 100 may additionally or alternatively employ any of a variety of other actuators, such as other mechanical actuators, electronic actuators, touch sensitive buttons, or the like.

FIGS. 4A-4B also show a lock mechanism 190 that may be included in or otherwise cooperate with the housing 112 be configured to lock the button 136 down or lock the piston 156 in a forward position. In the example shown, the lock mechanism 190 includes a tab 189 on the button 136 that can be slide into a corresponding slot 187 on the housing 112 to hold the button 136 in a depressed position upon moving or sliding the tab. Positioning the moving tab 189 on the button may facilitate ergonomic one-handed operation, allowing the user to depress the button and operate the lock mechanism in one seamless movement. However, it is contemplated the tab is instead included on the housing 112, which can hold the button down with or without a slot on the button (e.g., the tab can slide on top of the button when the button is depressed to avoid a need for a button slot). It is also contemplated that various other lock mechanisms may be suitably used. For example, the lock mechanism 190 can have a stop member disposed on the piston 156 (e.g., on an exterior surface thereof), a groove for accommodating the stop member when in an unlocked or biased position, and twistable member on the handle that is twistable relative to an axis of the piston 156. Twisting the twistable member may move the lock groove out of position where it can accommodate the stop member and cause the stop member to abut a surface and hold the piston in a forward position.

Figure 5A:
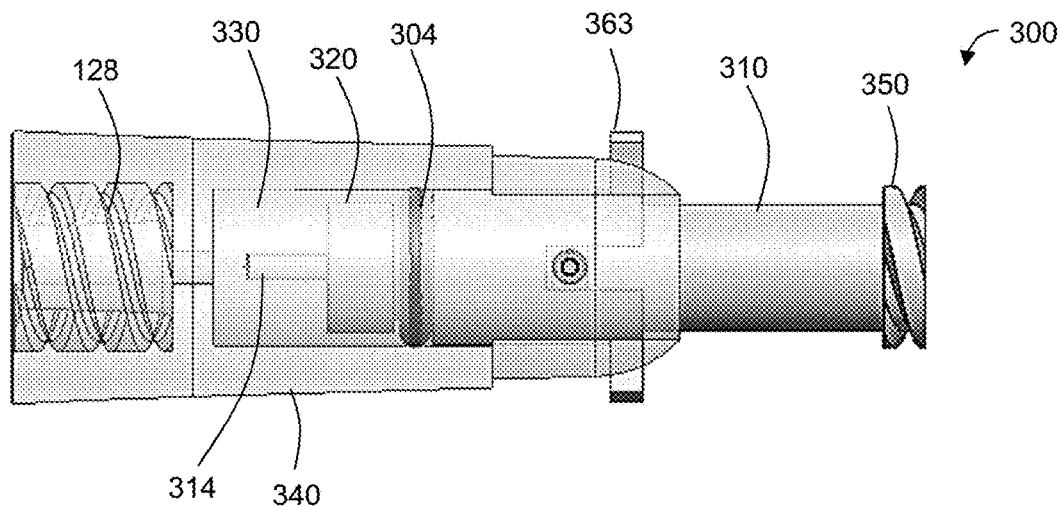
FIGS. 5A-5G illustrate various views of an example of a pre-fill component of a medical instrument.
Figure 5B:
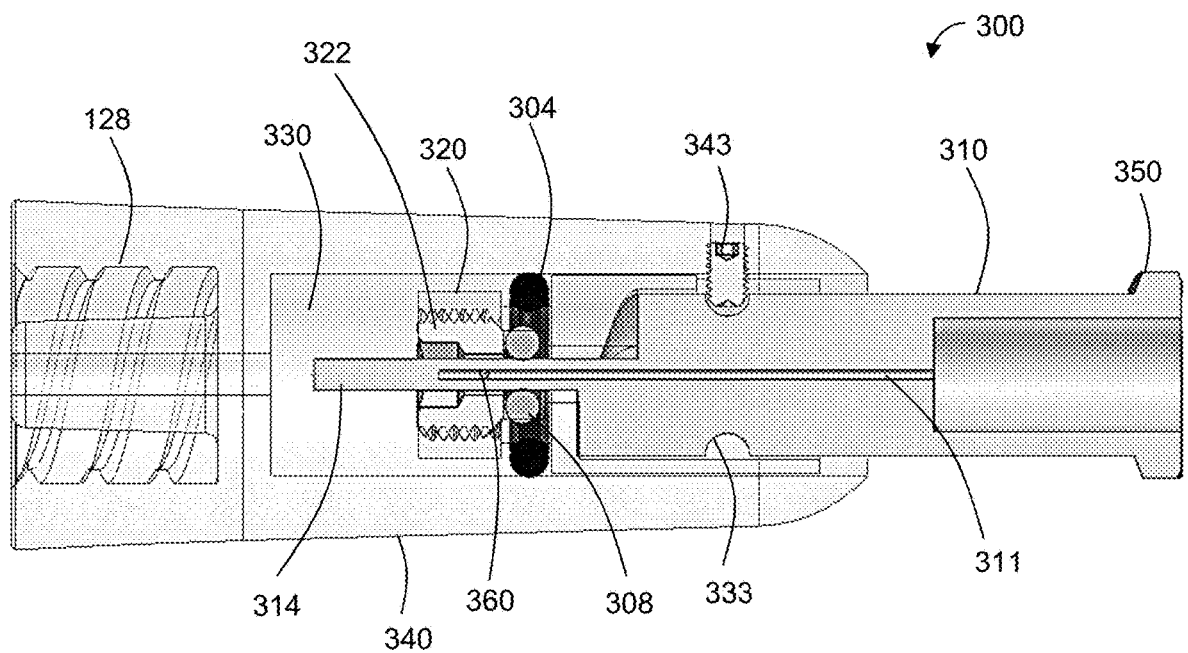
Figure 5C:
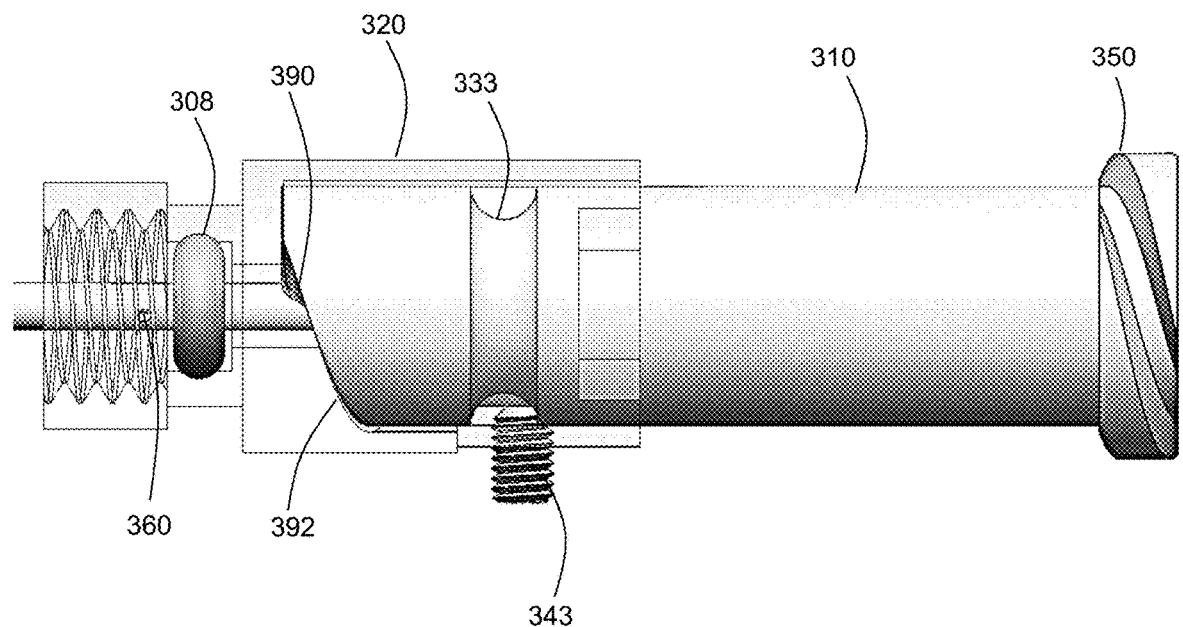
Figure 5D:
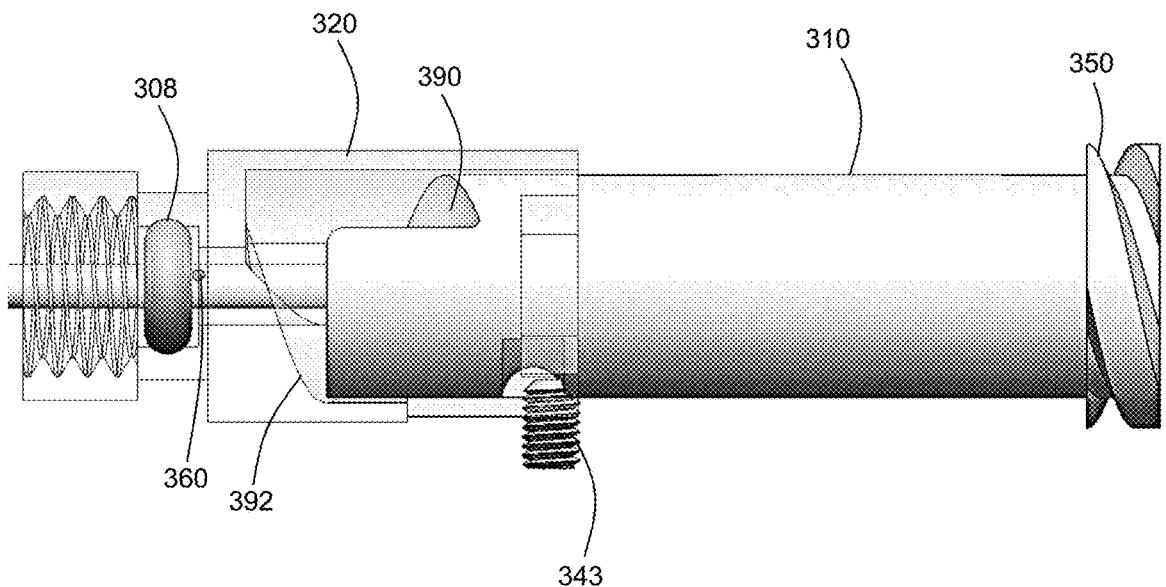
Figure 5E:
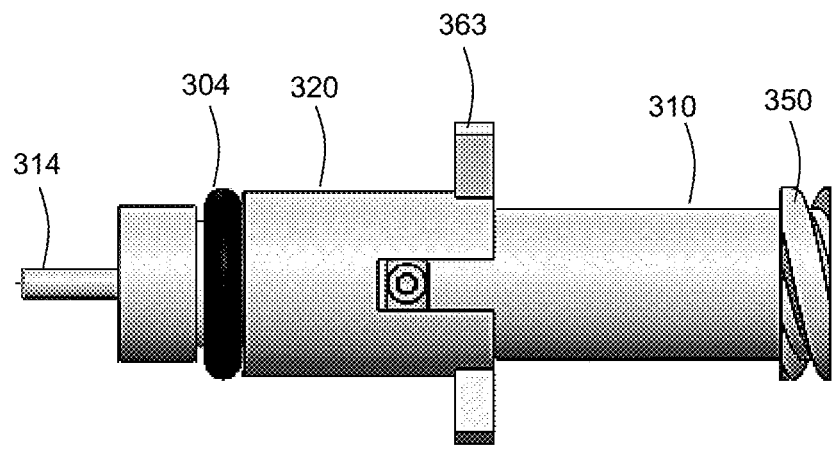
Figure 5F:
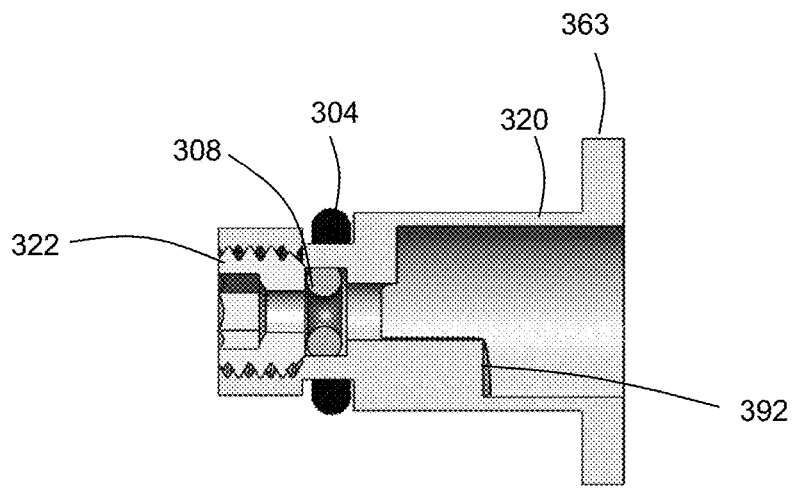
Figure 5G:
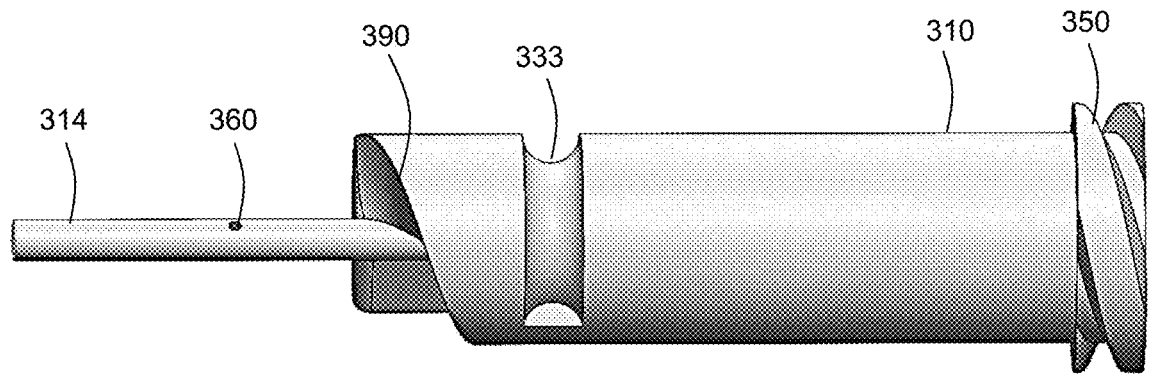

FIGS. 5A-5G illustrate various views of an example of a pre-fill component 300 that can be included in the medical instrument 100. FIG. 5A is a side view and FIG. 5B is a longitudinal cross-section view showing the pre-fill component coupled to the handle of the instrument. FIGS. 5C-5D are side views of the pre-fill component showing movement of a sliding seal at various stages of operation. FIGS. 5E-5G show various views of sub-components of the pre-fill component 300 in unassembled configurations.

As seen in the figures, the pre-fill component 300 can contain a pre-fill chamber 330 that provides a fluid compartment from which the fluid transfer mechanism can draw fluid. The pre-fill chamber 330 can be filled with a desired fluid by coupling a syringe 124 or other fluid source to the pre-fill component during a priming or initial stage prior to a procedure. The syringe may be then removed once the pre-fill chamber 330 is filled. The pre-fill component 300 may be useful to, for example, reduce a total length of the instrument 100 by allowing the fluid transfer mechanism to draw fluid from a smaller sized or lower volume fluid compartment than in configurations where the syringe or other larger fluid source is maintained attached to the device during a medical procedure.

Referring to FIGS. 5A-5B, the pre-fill component 300 can have a chamber body 340 that is coupled to the handle 104 and to the fluid transfer mechanism via an interface such as luer lock connector 128. For example, the pre-fill component 300 can be coupled to the housing 112 via luer lock connector 128 in a manner similar to how the syringe 124 can be coupled to the luer lock connector 128 in embodiments where the syringe 124 is directly coupled to the handle (e.g., as seen in FIG. 1A). It is also contemplated that the pre-fill chamber body 340 may be an integral part of the handle 104 or may otherwise be fixedly coupled to the handle.

The pre-fill component 300 can also include another luer connector 350 (e.g., at a proximal end thereof) for connecting to the syringe 124 or other fluid source that is used to fill the pre-fill component with the desired volume of fluid. For example, the syringe 124 may be attached to the pre-fill component 300 via luer connector 350, and the plunger 120 of the syringe may be depressed to first fill the pre-fill chamber 330 with a volume of fluid. Further depression of the plunger 120 may be used to bypass the mechanism as described above (e.g., to fully prime the instrument).

The pre-fill component 300 includes a mechanism to maintain a seal within the pre-fill chamber 330 upon removal of the syringe. The mechanism may be useful to, for example, avoid the potential introduction of air bubbles within the chamber or mitigate other undesirable effects upon removal of the syringe. FIGS. 5C-5D illustrate an operation of the mechanism of the pre-fill component 300 before and after detachment of a fluid source, such as syringe 124 (detached syringe not visible in FIGS. 5C-5D). FIGS. 5E-5G show various sub-components of the pre-fill component 300 that can be used to fill and seal the pre-fill chamber 330. These sub-components are also shown in various assembled configurations in FIGS. 5A-5D.

The pre-fill component 300 can include a sealing member 320 and an interface member 310. The sealing member 320 is configured to seal the pre-fill chamber 330 and permit the pre-fill chamber 330 to be filled via a fill port 360 of the interface member 310. The interface member 310 provides an interface between the pre-fill chamber 330 and the syringe used to fill the pre-fill chamber, which can be attached to the connector 350 of the interface member 310. The mechanism can be positioned as shown in FIG. 5C (and FIG. 5B) during delivery of fluid into the pre-fill chamber 330, where the fill port 360 is in fluid communication with the pre-fill chamber 330. The mechanism can be configured to then move the interface member 310 and the sealing member 320 apart from each other upon detachment of the syringe, to isolate the fill port 360 from the pre-fill chamber 330, as shown in FIG. 5D.

The pre-fill component 300 can be configured as follows to facilitate isolation of the fill port 360. The sealing member 320 can be slidably disposed in the chamber body 340, such that it can translate axially along a longitudinal axis thereof (which can correspond to the longitudinal axis 160 of the handle). The sealing member 320 can be configured to seal the chamber, for example, via an outer O-ring 304 that is coupled between an outer surface of the sealing member 320 and an inner surface of the chamber body 340. The outer O-ring 304 can be fixed to an outer surface of the sealing member 320 or the inner surface of the chamber body 340.

The sealing member 320 can also be rotatably fixed with respect to the chamber body 340 and the handle. For example, the sealing member 320 can include one or more anti-rotation tabs 363, which can protrude radially outward from the sealing member 320. The anti-rotation tabs 363 can be slotted in longitudinal slots of the chamber body 340 to constrain rotational movement of the anti-rotation tabs 363 about the longitudinal axis against the longitudinal slots, while permitting axial translation of the anti-rotation tabs 363 along the longitudinal slots. It will be appreciated that this configuration can be reversed, such that the anti-rotation tabs 363 are included on the chamber body and protrude radially inward into longitudinal slots of the sealing member 320. Various other mechanisms can be used to constrain the movement as desired.

The interface member 310 includes the connector 350 at its proximal end for coupling to the fluid source, and a projection 314 at its distal end that extends through an opening in the sealing member 320. The fill port 360 is disposed on the projection 314, and configured as a side port positioned on a lateral side of the projection 314 proximal to the terminal end at the distalmost end of the projection 314. This configuration allows an inner O-ring 308, disposed between an inner surface of the sealing member 320 and an outer surface of the projection 314, to pass over the fill port 360 with relative movement between the sealing member 320 and the interface member 310, thereby sealing the fill port 360 from the pre-fill chamber 330 or permitting the fill port 360 to fluidly communicate with the pre-fill chamber 330 depending on the relative positions of the sealing member 320 and interface member 310. The fill port 360 can be coupled to the luer connector 350 via a lumen 311 extending partially through the interface member 310. The inner O-ring can, for example, be held in place via a hollow set screw 322 of the sealing member, located on a distal side of the inner O-ring 308, which can permit the projection 314 to extend therethrough. Alternatively, any other suitable mechanism can be used to hold the inner O-ring in place, such as, for example, a circumferential groove along the inner surface of the sealing member 320.

The interface member 310 can be translatably fixed relative to the handle and chamber body via a retention groove 333. A guide member 343, such as a set screw, can be positioned in the retention groove 333, and the retention groove can be configured as a circumferential groove on an outer surface of the interface member 310 to permit the rotation of the interface member 310 as the guide member slides along the circumferential groove. The retention groove 333 can have stops positioned at ends thereof that permit rotation of the interface member 310 within only a limited range of motion, such as 180 degrees, which corresponds to half of a circumference of the outer surface of the interface member 310, but prevent rotation of the interface member beyond that limited range of motion upon the guide member 343 abutting the stop at the end of the groove. It will be appreciated that this can be tuned to any other limited range of rotation desired.

Each of the sealing member 320 and the interface member 310 include complementary spiral ramps 390, 392, which are configured to mate with each other. For example, sealing member 320 can include a first spiral ramp 392 facing a proximal direction, and the interface member 310 can include a second spiral ramp 390 facing a distal direction. The mating spiral ramps are configured to urge the interface member 310 and the sealing member 320 apart from each other with relative rotation therebetween, thereby sliding the inner O-ring over the fill port 360 to isolate the fill port 360 from the pre-fill chamber. For example, as the mated spiral ramps 390, 392 slide over each other with rotation of the interface member 310, the longitudinal translation constraint of the interface member coupled with the rotational constraint of the sealing member 320 causes the spiral ramp 390 of the interface member 310 to drive the sealing member 320 in a distal direction to thereby slide the inner O-ring 308 over the fill port 360, as seen in FIG. 5D.

An operation of the pre-fill component may thus be as follows. First, a user may attach a syringe to the luer connector 350 of the interface member 310, by rotating the syringe about the longitudinal axis in a first direction (e.g., clockwise). The guide member 343 may abut against a first stop at a first end of the circumferential retention groove 333 to permit the syringe to be tightened against the luer connector 350 as it is rotated in the first direction.

Next, the user may depress the plunger of the syringe to deliver fluid into the pre-fill chamber 330 through the luer connector. The user may further depress the plunger to prime the fluid transfer mechanism downstream from the pre-fill chamber after the pre-fill chamber has been filled, where depression of the plunger bypasses the check valves in the fluid transfer mechanism.

Once the instrument is primed, the user may begin to remove the syringe by rotating the syringe in a second direction, opposite the first direction (e.g., counter-clockwise). The rotation to remove the syringe may have two phases.

During the first phase, the interface member 310 rotates together with the syringe, as the guide member slides along the retention groove away from the first stop, along the groove, and towards the second step. As the interface member 310 rotates about the longitudinal axis together with the syringe, the spiral ramp 392 of the interface member urges movement of the sealing member 320 distally along the longitudinal axis, causing the interface member 310 and the sealing member 320 to separate from each other until the inner O-ring 308 slides past the fill port 360 to isolate the fill port 360 from the pre-fill chamber 330, and thus isolate the pre-fill chamber 330 from the syringe. As the syringe has been rotating together with the interface member 310 thus far, the seal between the syringe and the luer connector 350 remains intact and no air is introduced into the device.

After the inner O-ring passes over the fill port 360, the interface member 310 reaches the end of its limited rotational travel as the guide member 343 abuts the second stop at the opposite end of the retention groove 333 from the first stop. After this, the second phase of rotation is reached. During this second phase, the further rotation of the syringe disconnects the syringe from the luer connector 350 of the interface member, as the interface member is constrained from further rotation by the second stop. As the fill port 360 is now isolated from the pre-fill chamber, any air introduced by the disconnection of the syringe is prevented from reaching the pre-fill chamber.

Finally, after the syringe has been removed, the user (e.g., surgeon or medical practitioner) may operate the fluid transfer mechanism to deliver doses of fluid from the pre-fill chamber. The sealing member 320 may operate as a plunger at this stage, where each dosage of fluid caused by actuating the button draws the sealing member 320 forward distally by an amount of one dosage volume unit.

Figure 6:
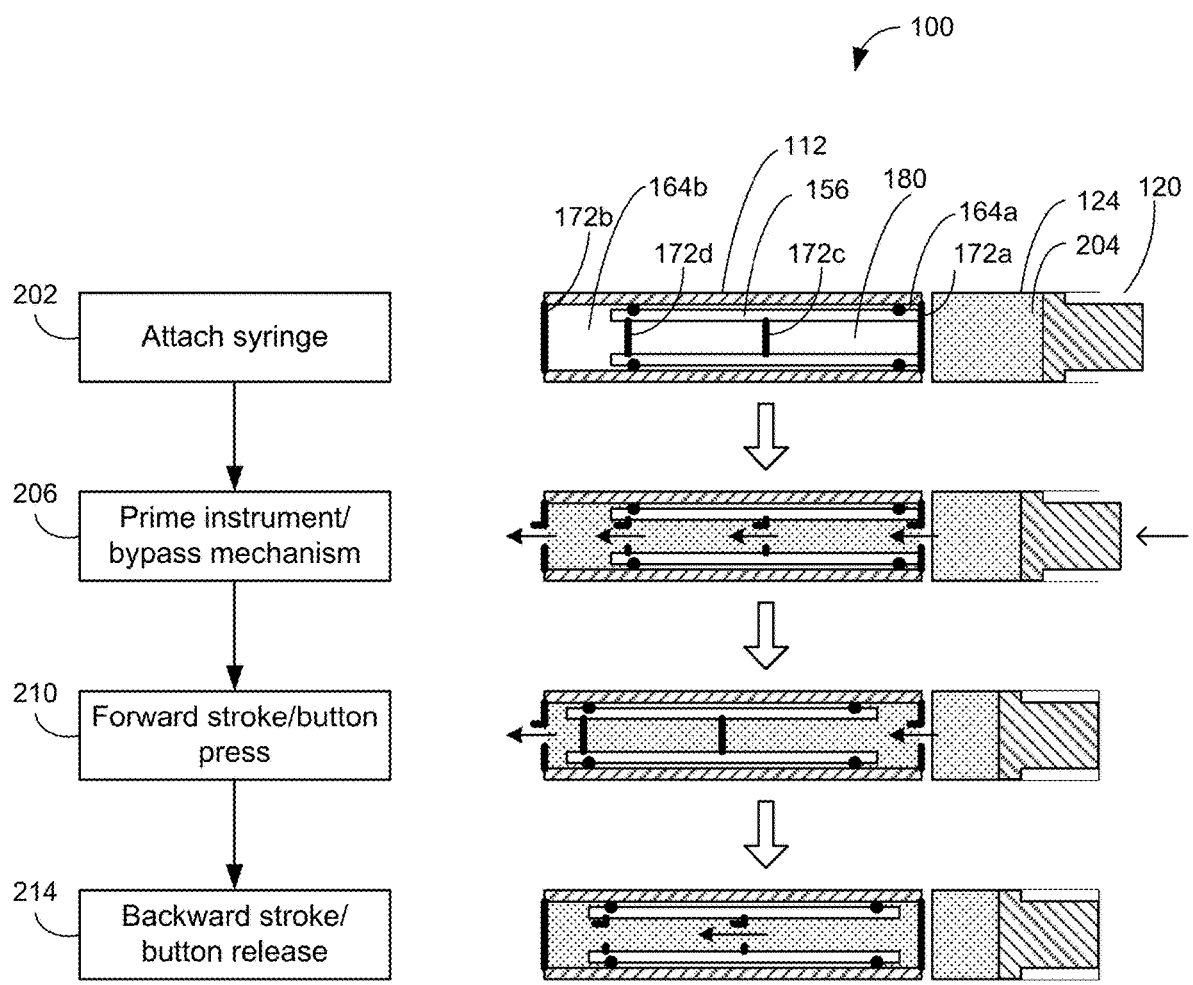
FIG. 6 illustrates a flow chart of an example of a method of operating a medical instrument.

Referring now to FIG. 6, an example method of operation is depicted. FIG. 6 shows a process flow and a schematic diagram of the surgical instrument 100 with various details omitted for simplicity. In FIG. 6, valves 172a-d are depicted schematically as open or closed during each stage, with corresponding arrows depicting a direction of fluid flow across the valve where appropriate.

At step 202, a user may attach a syringe 124 to the housing 112. The syringe 124 may be attached using a luer lock connector or other suitable connection interface, as described above. At this stage, the fluid transfer mechanism is in a steady state and no fluid is flowing through the fluid transfer mechanism.

At step 206, a user may prime the instrument 100. In particular, the plunger 120 of the syringe 124 may be depressed, or fluid 204 may otherwise be ejected from the syringe 124, which may cause a cracking pressure of each of the valves 172a-d to be exceeded and cause fluid to flow through each of the valves 172a-d, and through the entire housing 112, in the forward direction. Once fluid is ejected from the tool or tip of the instrument, air bubbles may be removed and the instrument may be primed for fluid delivery to the intended target site, as appropriate. Additionally or alternatively, a similar process of depressing the plunger 120 may be used to bypass the fluid transfer mechanism and deliver a steady dosage of fluid, as desired. In particular, a cracking pressure of each of the valves 172a-d may be configured to be exceeded upon a depression of the plunger 120. In the example shown, the syringe 124 remains attached to the instrument during the remainder of the procedure to supply the fluid 204 delivered by the piston pump mechanism. In other embodiments, priming the instrument 100 may fill a pre-fill chamber as described herein. This may allow the syringe 124 to be removed at this stage, as fluid 204 delivered during the procedure via the piston pump mechanism can be drawn from the pre-fill chamber in the remaining steps.

At step 210, a user may press the button, or a forward stroke of the piston 156 may be otherwise actuated. As shown in FIG. 6, during the forward stroke of the piston 156 the entry chamber 164a may expand, generating a pressure differential or suction force across the entry valve 172a that exceeds its cracking pressure and causes fluid to be drawn into the entry chamber 164a from the fluid compartment. Simultaneously, or during the same forward stroke, the exit chamber 164b compresses, causing a cracking pressure of the exit valve 172b to be exceeded and causing fluid to be ejected from the chamber 164b. In this fashion, a dosage of viscoelastic fluid or other fluid may be delivered to a blade, or other surgical tool, or otherwise delivered to a target site. Since the piston valves 172c,d restrict entry to only the forward direction, they remain closed during the forward stroke and facilitate compression and expansion of the chambers 164a,b, as described above.

At step 214, a user may release the button, or a backward stroke of the piston 156 may be otherwise initiated. As shown in FIG. 6, during the backward stroke of the piston 156 the exit chamber 164b expands and the entry chamber 164a compresses. At the same time, the piston valves 172c,d open and permit forward fluid flow across them, thus transferring fluid from the entry chamber 164a to the exit chamber 164b as the entry valve 172a and exit valve 172b remain closed. This may return the piston 156 to its biased position where it is ready to deliver another dosage of fluid.

It will be appreciated that embodiments disclosed herein may be useful for medical and surgical procedures. There are numerous medical and surgical procedures in which it is desirable to cut and remove a strip of tissue of controlled width from the body of a human or veterinary patient. For example, it may sometimes be desirable to form an incision of a controlled width (e.g., an incision that is wider than an incision made by a typical scalpel, cutting blade or needle) in the eye, skin, mucous membrane, tumor, organ or other tissue or a human or animal. In addition, it may sometimes be desirable to remove a strip or quantity of tissue from the body of a human or animal for use as a biopsy specimen, for chemical/biological analysis, for retention or archival of DNA identification purposes, etc. In addition, some surgical procedures require removal of a strip of tissue of a known width from an anatomical location within the body of a patient.

One surgical procedure wherein a strip of tissue of a known width is removed from an anatomical location within the body of a patient is an ophthalmological procedure used to treat glaucoma. This ophthalmological procedure is sometimes referred to as a goniotomy. In a goniotomy procedure, a device that is operative to cut or ablate a strip of tissue of approximately 2-10 mm in length or more and about 50-230 µm in width is inserted into the anterior chamber of the eye and used to remove a full thickness strip of tissue from the trabecular meshwork. The trabecular meshwork is a loosely organized, porous network of tissue that overlies a collecting canal known as Schlemm's canal. A fluid, known as aqueous humor, is continually produced in the anterior chamber of the eye. In healthy individuals, aqueous humor flows through the trabecular meshwork, into Schlemm's canal and out of the eye through a series of ducts called collector channels. In patients who suffer from glaucoma, the drainage of aqueous humor from the eye may be impaired by elevated flow resistance through the trabecular meshwork, thereby resulting in an increase in intraocular pressure. The goniotomy procedure can restore normal drainage of aqueous humor from the eye by removing a full thickness segment of the trabecular meshwork, thus allowing the aqueous humor to drain through the open area from which the strip of trabecular meshwork has been removed.

Embodiments disclosed herein can be used for surgical medicinal intervention. For example, some embodiments relate to a microsurgical device and methods of its use for treatment of various medical conditions including but not limited to eye diseases, such as glaucoma, using minimally invasive surgical techniques. In some embodiments, the device may be a dual-blade device for cutting the trabecular meshwork ("TM") in the eye. For example, the device may have a device tip providing entry into the Schlemm's canal via its size (i.e., for example, between approximately 0.2-0.3 mm width) and a configuration where the entry blade tip ramps upwardly providing a wedge or ramp-like action for cutting the TM. Alternatively, a single incision device tip such as a microvitreoretinal ("MVR") blade (BD, Franklin Lakes, New Jersey, USA) or a cautery device tip such as a Trabectome® device may be used. In some embodiments, the tool section 102 of the device can include a cannula, a microcannula, or dual-blade tool having a lumen for delivering fluid such as, for example those described in U.S. Non-Provisional application Ser. No. 15/791,204, filed on Oct. 23, 2017, U.S. Non-Provisional application Ser. No. 15/389,328, filed on Dec. 22, 2016, U.S. Provisional Application No. 62/750,151, filed on Oct. 28, 2018, or U.S. Non-Provisional application Ser. No. 15/847,770, filed on Dec. 19, 2017, the entirety of each of which is incorporated herein by reference.

Figure 7:
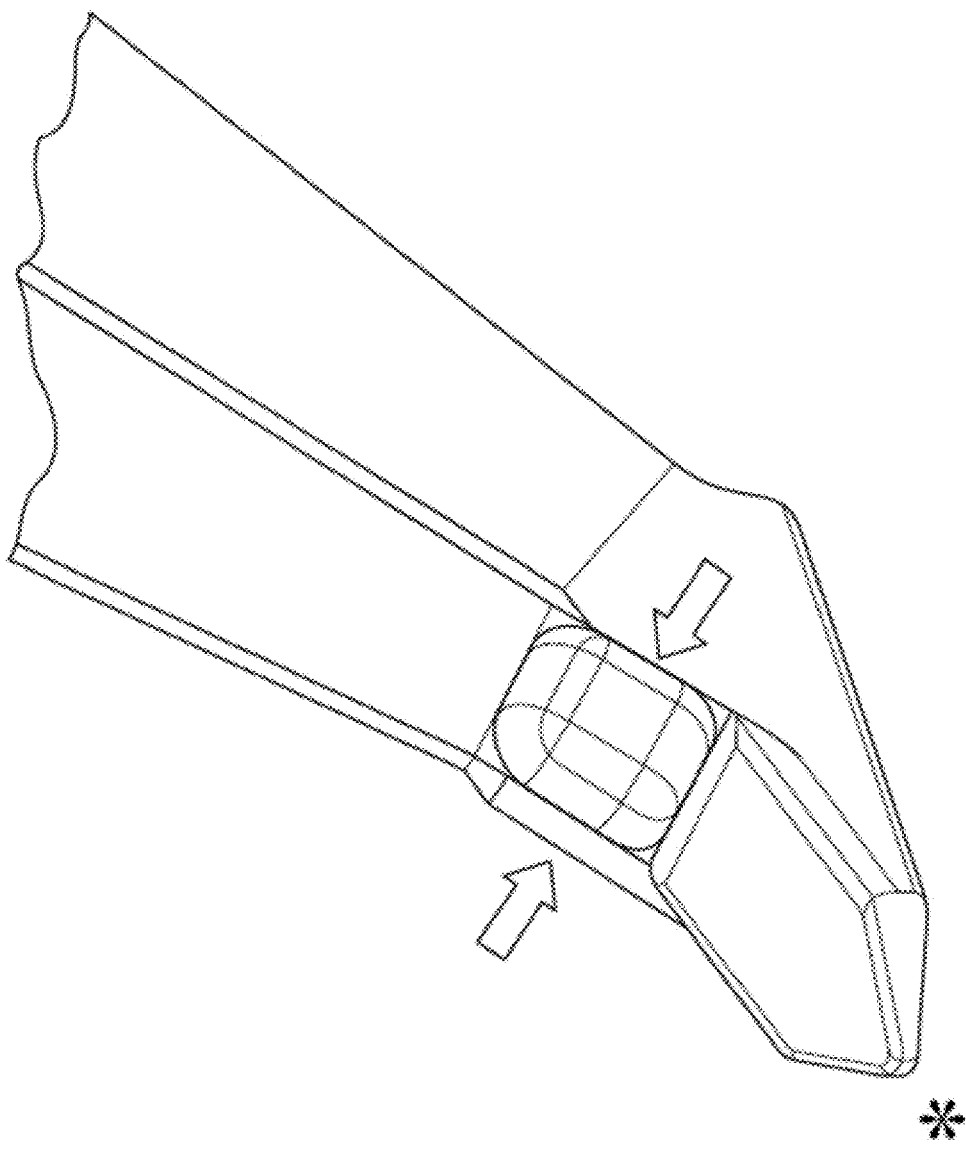
FIG. 7 illustrates an isometric view of an example of an ophthalmic blade having a lumen.

Turning now to FIG. 7, an example dual blade tool for treatment of glaucoma is illustrated. In some embodiments, the tool may be included in the tool section 102 of the instrument 100. In particular, the tool is illustrated to reveal the dual cutting blades (arrows) as well as the distal point (asterisk) that is designed to pierce the trabecular meshwork ("TM") and enter into the Schlemm's canal. Once in the canal, the tool is advanced so that the TM moves up the ramp from the distal point toward the dual cutting blades, which then cleanly incise the presented TM. The distance between the dual blades is designed to closely match that of the width of the TM across a range of human eyes.

Figure 8:
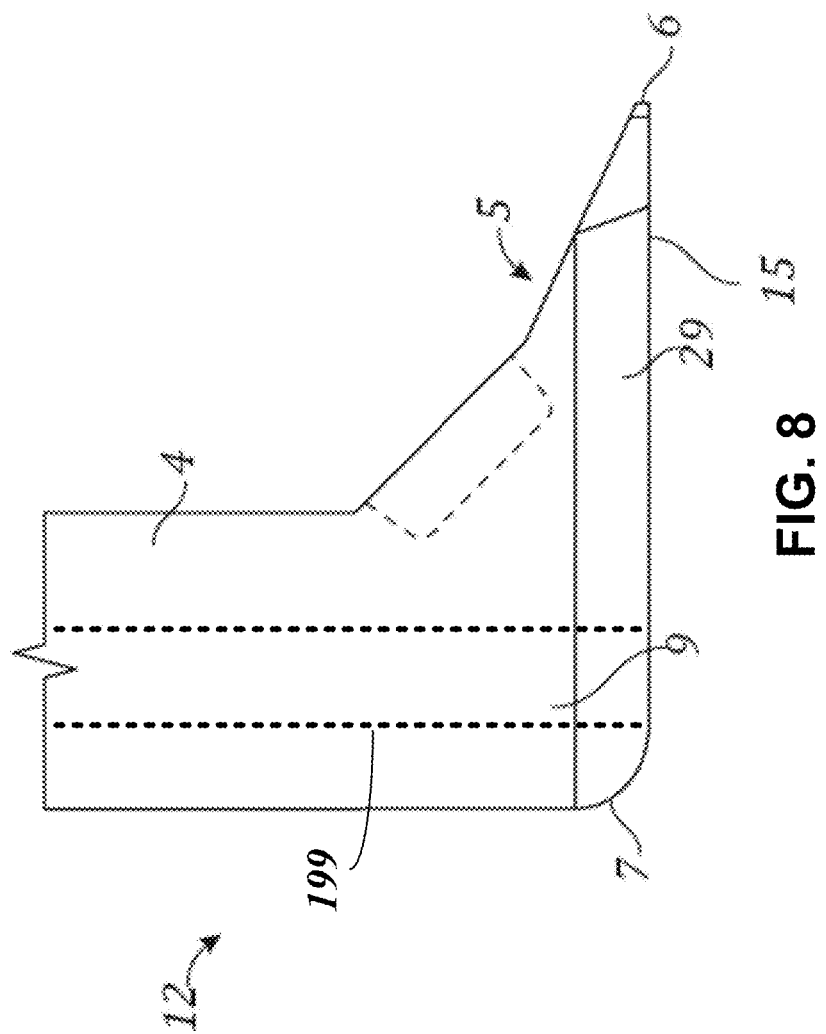
FIG. 8 illustrates a side view of an example of an ophthalmic blade having a lumen.
Figure 9:
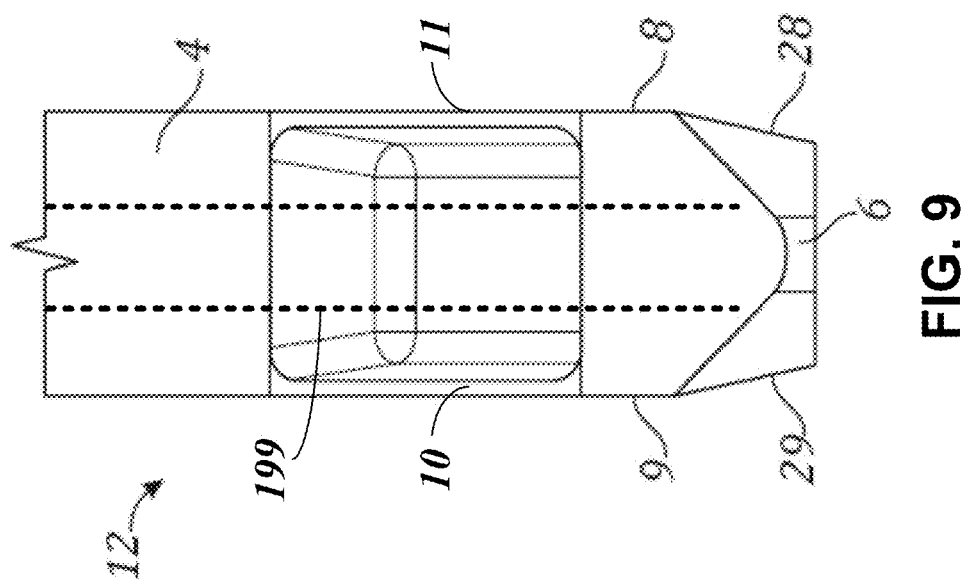
FIG. 9 illustrates a front view of an example of an ophthalmic blade having a lumen.
Figure 10:
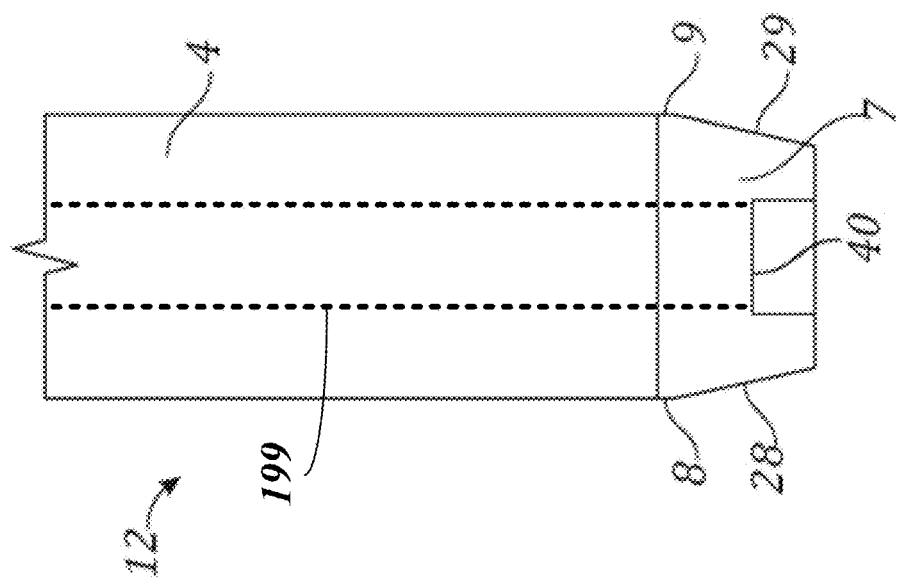
FIG. 10 illustrates a rear view of an example of an ophthalmic blade having a lumen.

Referring now to FIGS. 8-10, a device 12 is shown. In some embodiments, the device 12 may be implemented as an ophthalmic blade that can be included in a distal end of the tool section 102 of the instrument 100 described above. The device 12 may further include a lumen 199 that provides a fluidic pathway for delivery or injection of fluid received from a fluid transfer mechanism included in a handle 104. As shown in FIG. 8, a platform 5 of the device 12 can include a tip 6 at a distal side of the platform 5 and a top surface (e.g., ramp) 13 extending from the distal side of the platform 5 to a proximal side of the platform 5, opposite the distal side of the platform 5. For example, the top surface 13 can extend from the tip 6 to one or more lateral elements 10, 11.

As further shown in FIG. 8, the platform 5 can include a bottom surface 15 extending from the tip 6 at the distal side of the platform 5 to a rear portion 7 of the platform 5, opposite the tip 6. The bottom surface 15 of the device 12 can be positioned opposite the top surface 13. The bottom surface 15 can be configured to abut the outer wall of the Schlemm's canal during a procedure (see FIGS. 15A-15C). At least a portion of the bottom surface 15 can be flat and/or planar. The rear portion 7 can define a curved or round surface that transitions from the bottom surface 15 to a portion of the shaft 4.

As shown in FIGS. 9 and 10, opposing sides 8, 9 of the platform 5 can extend downwardly from the top surface 13. The opposing sides 8, 9 can be planar and/or parallel to each other. The top surface 13 can transition to the opposing sides 8, 9 with a transition feature. While a round bevel is shown in FIGS. 8-10, the transition feature can have one or more other shapes, including curved, round, chamfer, fillet, etc.

A transition feature can be provided between the bottom surface 15 and the opposing sides 8, 9. For example, the bottom surface 15 can transition to the opposing sides 8, 9 with transition sections 28, 29, respectively. While chamfers are shown for transition sections 28, 29 in FIGS. 8-10, the transition feature can have one or more other shapes, including curved, round, beveled, fillet, etc. Along the transition features, the width of the device 12 can transition from a first width, between the opposing sides 8, 9, to a second width, less than the first width, across the bottom surface 15. The transition from the first width to the second width can be gradual, linear, stepwise, or another type of transition.

Figure 11:
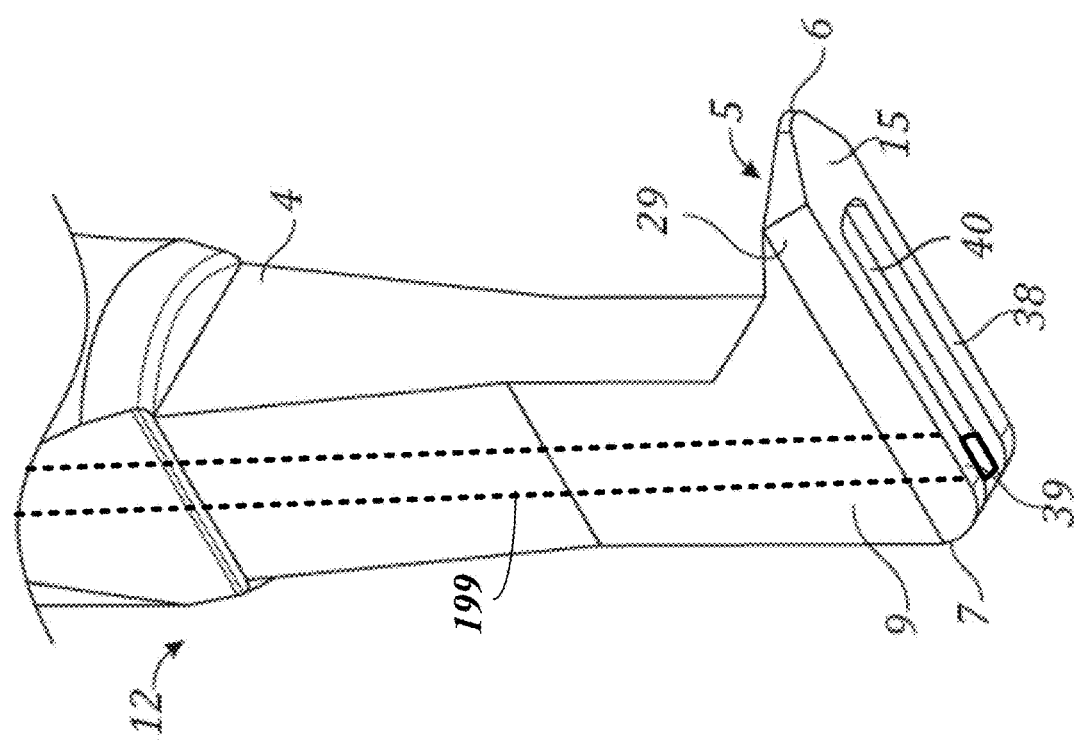
FIG. 11 illustrates an isometric view of an example of an ophthalmic blade having a lumen.
Figure 12:
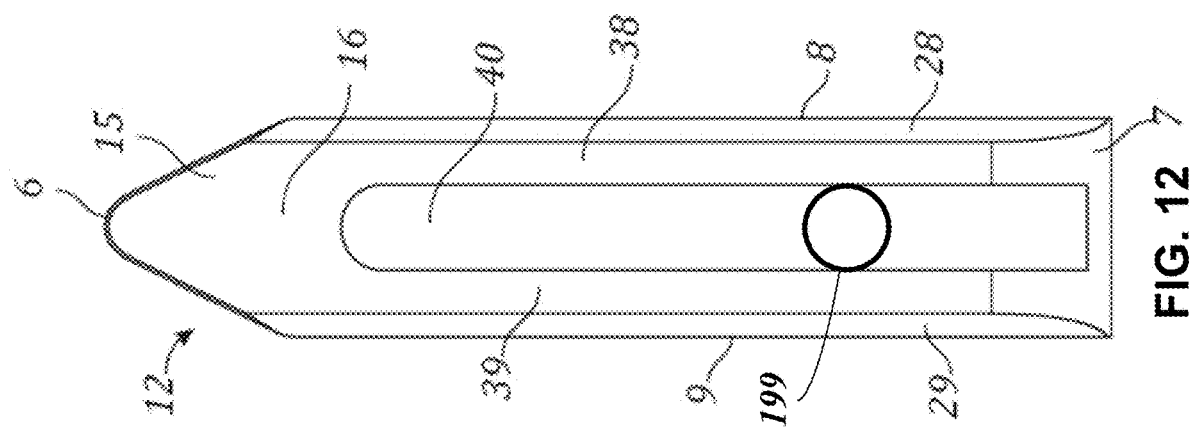
FIG. 12 illustrates a bottom view of an example of an ophthalmic blade having a lumen.

Referring now to FIGS. 10-12, the bottom surface 15 of the device 12 can include surface features that enhance interactions with the outer wall of the Schlemm's canal during a procedure. For example, the bottom surface 15 can be planar, convex, concave, or combinations thereof. By further example, as shown in FIGS. 11 and 12, the bottom surface 15 can include a recessed portion 40 between at least two protrusions. The recessed portion 40 can be defined by a gap, space, or void. A first protrusion 38 can be positioned below the first side 8 and/or the first transition section 28 of the platform 5. The first protrusion 38 can be formed, at least in part, by at least a portion of the first transition section 28. A second protrusion 39 can be positioned below the second side 9 and/or the second transition section 29 of the platform 5. The second protrusion 39 can be formed, at least in part, by at least a portion of the second transition section 29. Each of the protrusions 38, 39 can extend from the rear portion 7 of the platform 5 toward the tip 6. The protrusions 38, 39 can be separated by a recessed portion 40 extending there between. As shown in FIGS. 10 and 11, a transition between the protrusions 38, 39 and the recessed portion 40 can be stepwise, forming one or more edges. Additionally or alternatively, a transition between the protrusions 38, 39 and the recessed portion 40 can be gradual, curved, round, beveled, chamfered, linear, or another type of transition. For example, the recessed portion 40 can include a concave feature. The recessed portion 40 can extend to and intersect the rear portion 7 of the platform 5.

Adjacent to the tip 6, the bottom surface 15 can provide a continuous (e.g., planar) portion 16 that is not interrupted by the recessed portion 40. The tip 6 can be separated from the recessed portion 40 by the continuous portion 16. Accordingly, the bottom surface 15 can include a planar distal portion and a non-planar proximal portion along the length thereof. The tip 6 and the region (e.g., continuous portion 16) immediately proximal to the tip 6 can be continuous, such that the recessed portion 40 does not intersect the tip 6. The recessed portion 40 can extend distally from the rear portion 7, for example, not farther than the opposing sides 8, 9 and/or the transition sections 28, 29. As shown in FIG. 12, the recessed portion 40 can terminate on a distal end thereof with a transition feature that is, for example, gradual, curved, round, beveled, chamfered, linear, stepwise, or another type of transition.

The planar distal portion can provide an even surface to facilitate entry into tissue with the tip 6. The nonplanar proximal portion (e.g., the protrusions 38, 39 and the recessed portion 40) can interact with the Schlemm's canal during a procedure. As the platform 5 is moved, at least some of the tissue can be received within the recessed portion 40 between the protrusions 38, 39. The protrusions 38, 39 provide a smaller surface area for exposure to the tissue (e.g., Schlemm's canal). Accordingly, the nonplanar proximal portion of the bottom surface 15 provides greater maneuverability of the platform 5 as it moves along the tissue.

Figure 13:
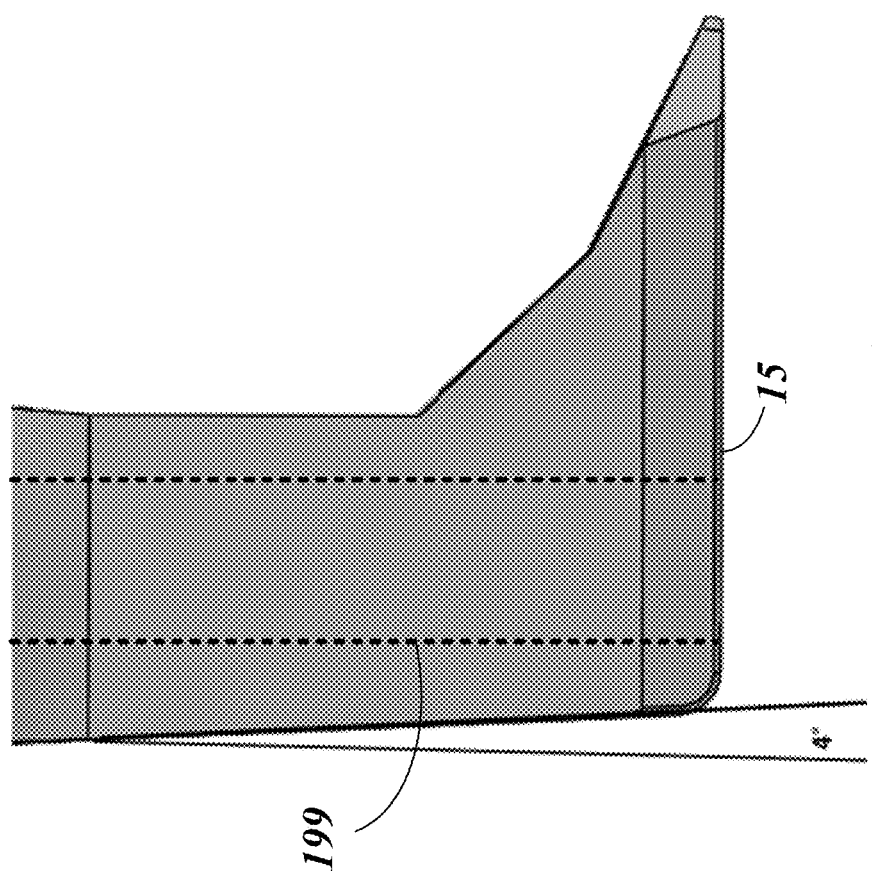
FIG. 13 illustrates a side view of an example of an ophthalmic blade having a lumen.

Referring now to FIG. 13, a cross section view of a device similar in some respects to that shown in FIGS. 8-12 is depicted. The device further includes an angle (e.g., 4 degrees) on a vertical shaft that allows for a lumen 199 down the shaft. In particular, the angle between the bottom surface 15 and a back surface of the platform 5 is obtuse, and the back surface is positioned approximately 4 degrees apart relative to a normal of the bottom surface.

Figure 14:
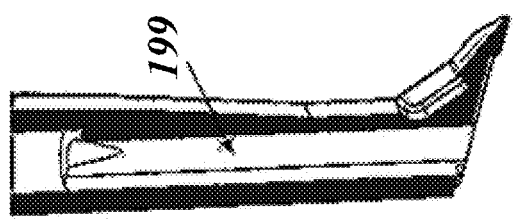
FIG. 14 illustrates a side view of an example of an ophthalmic blade having a lumen.

Referring now to FIG. 14, a cross section view of a device is depicted. In particular, the device is a tool containing an ophthalmic blade of a type similar to those described above with reference to FIGS. 8-13. The device further includes a lumen 199 that may be used for fluid delivery. For example, the lumen 199 may be configured to receive viscoelastic fluid from a fluid transfer mechanism and deliver the viscoelastic fluid to a trabecular meshwork or otherwise inject fluid to an intraocular cavity.

FIGS. 15A-15D illustrate an example device and method of operation that may be employed in some embodiments of the instrument 100. In particular, FIGS. 15A-15D show operation of an ophthalmic blade that may be integrated in the tip of the tool section 102 (see, e.g., FIG. 1) and applied to a trabecular meshwork. FIGS. 15A-15D also show a lumen 199 that may be used for fluid delivery during the method.

The device may be introduced through a clear corneal incision on an eye (e.g., incision size between 0.5 and 2.8 mm in width) and advanced through an anterior chamber of the eye, either across the pupil or across the body of the iris to engage the trabecular meshwork (TM) on the opposite side of the anterior chamber. The anterior chamber is filled with aqueous humor and, by way of example, may have a volume of approximately 0.25 milliliter (ml) and be approximately 3 millimeter (mm) deep. The anterior chamber may be filled with viscoelastic to replace the aqueous humor and stabilize the chamber during the procedure. Accordingly, approximately 0.25 ml may be injected into the chamber at this stage of the surgery. The viscoelastic may be injected into the anterior chamber using a syringe. In some embodiments, the viscoelastic may be injected by depressing plunger 120 or otherwise ejecting fluid from the syringe 124 in a manner that bypasses a fluid transfer mechanism in the instrument 100 (see FIGS. 1-6) and causes fluid to flow through the lumen 199. Additionally or alternatively, actuation of the fluid transfer mechanism (e.g., via button 136) may be used. In some embodiments, each button press may be configured to deliver only a small single dosage of fluid (e.g., approximately 0.03 to 0.05 ml of viscoelastic with each button press). In these cases, the bypass mechanism may be useful for allowing the anterior chamber to be initially filled with a larger volume of viscoelastic without a need for a separate syringe. Further, this may allow the fluid transfer to be used later during the procedure to deliver smaller dosages as appropriate, without a need for the surgeon to change their grip during operation.

Figure 15A:
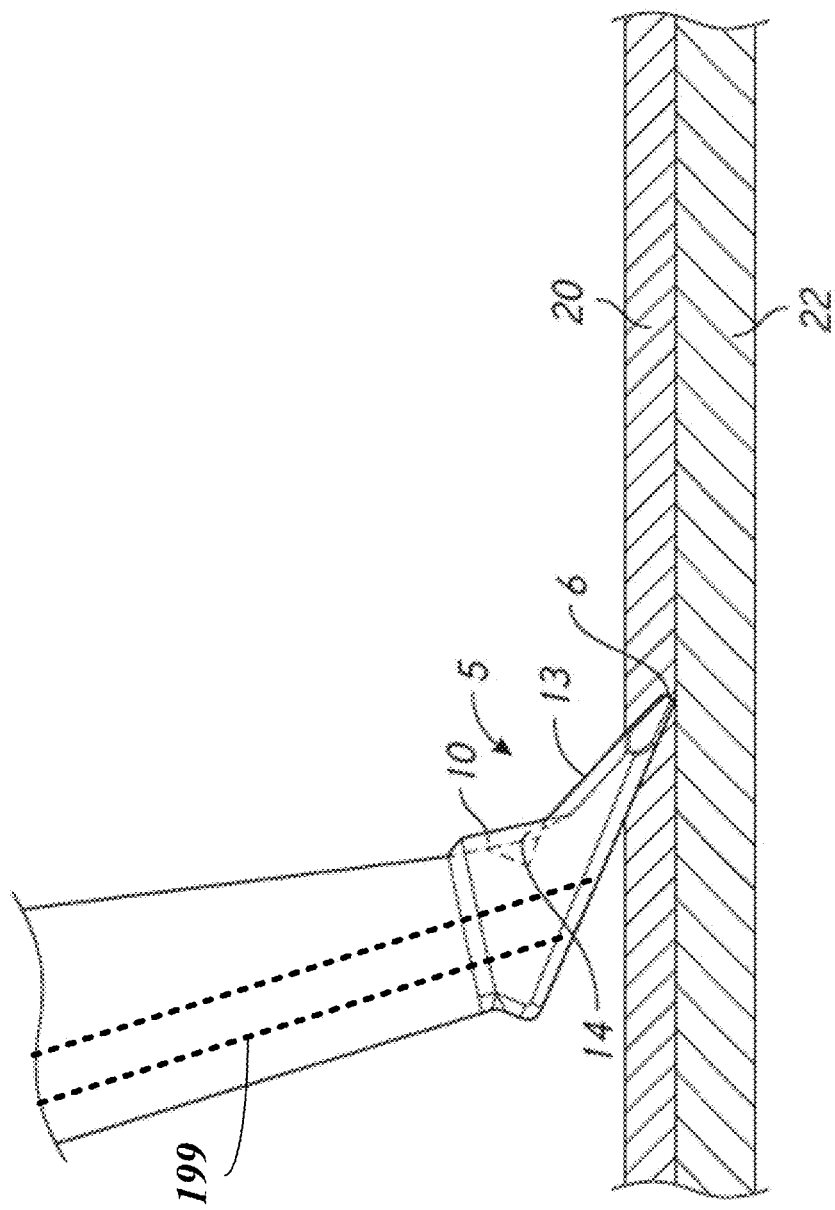
FIGS. 15A-15D illustrate a process flow of an example of a method of operation.
Figure 15B:
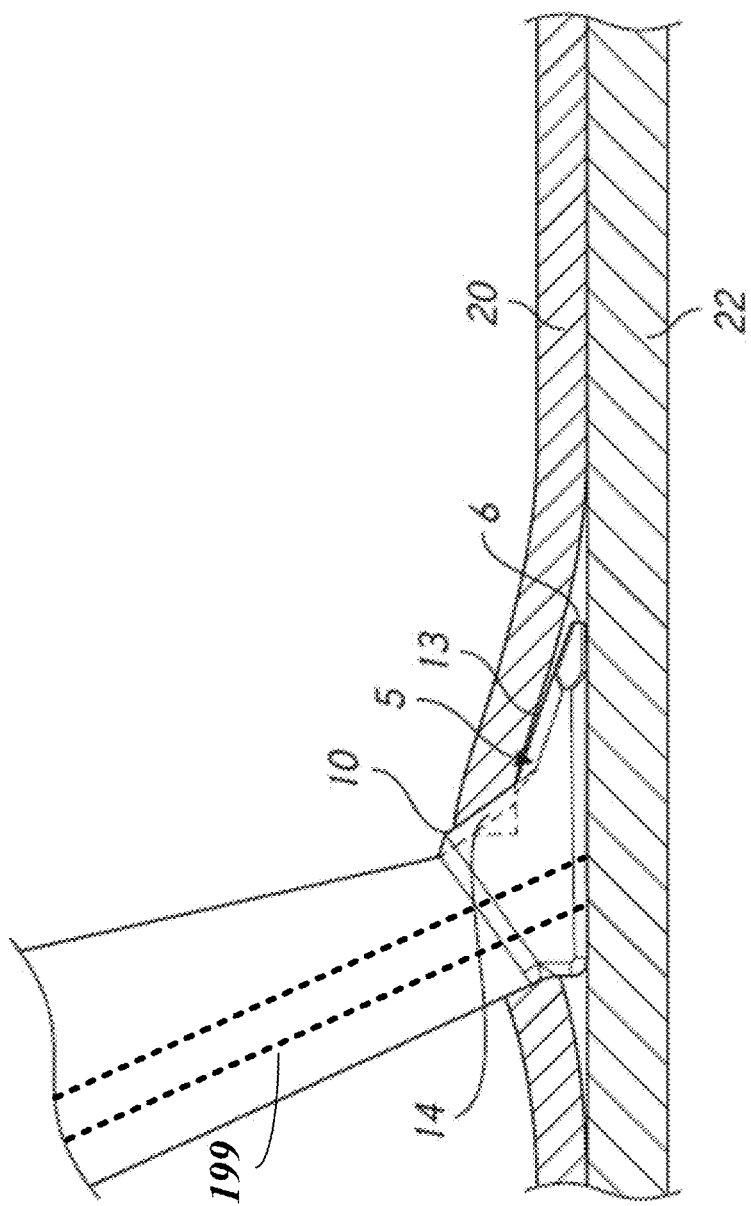
Figure 15C:
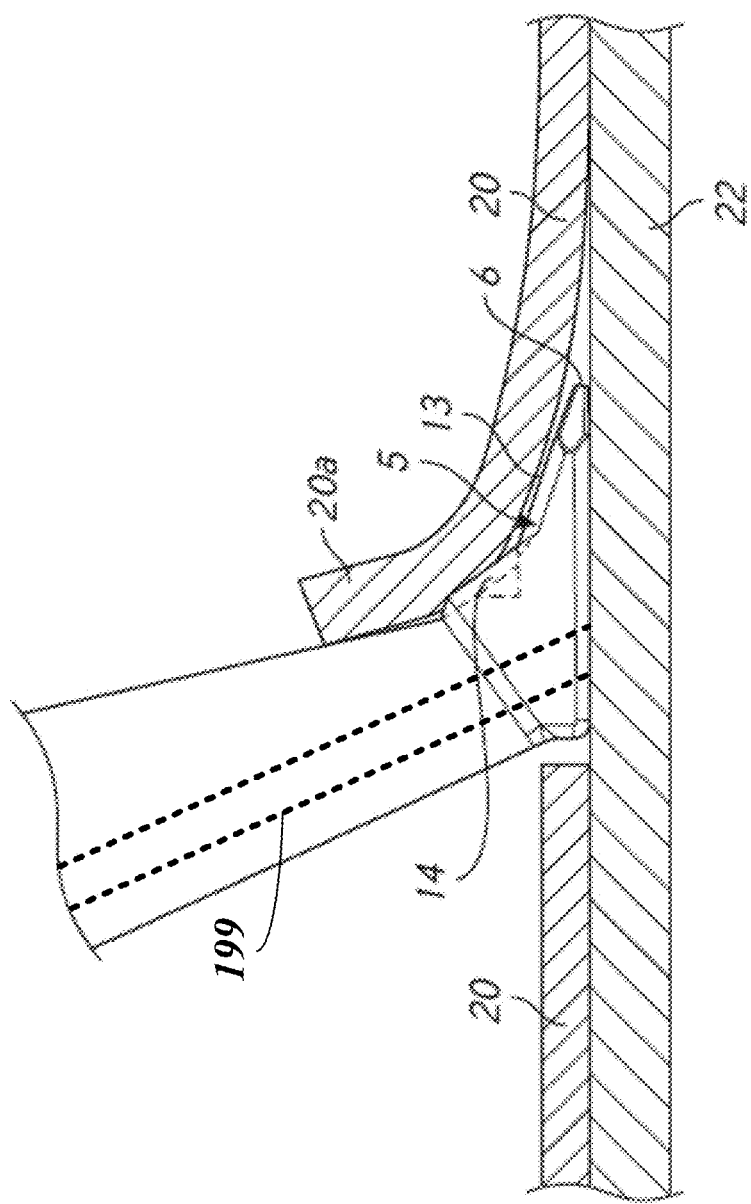
Figure 15D:
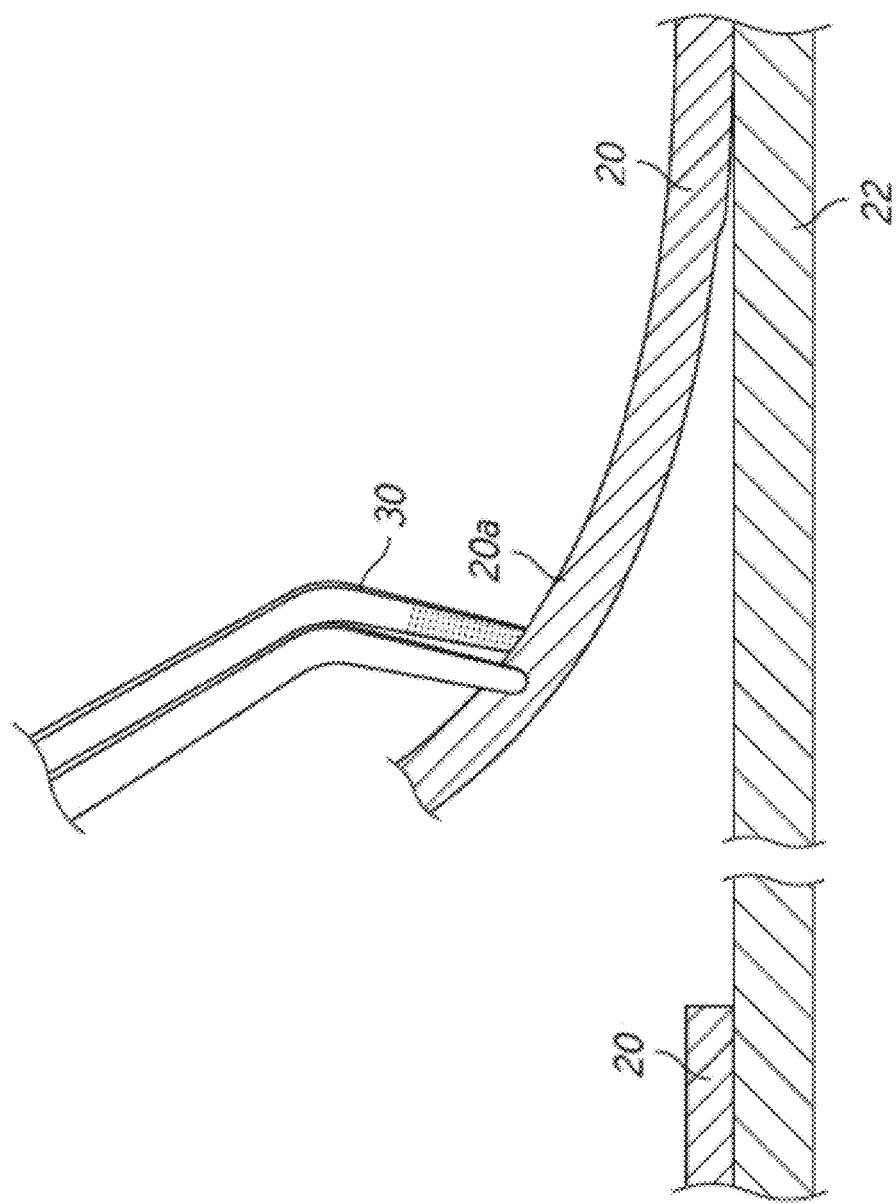

As shown for example in FIG. 15A, once the target tissue 20 (e.g., TM) is reached, the tip 6 of the device may be then used to enter into Schlemm's canal ("SC") 22. According to some embodiments, for example as shown in FIG. 15A, the ramp 13 may be used to elevate the TM 20 away from the outer wall of the Schlemm's canal 22. According to some embodiments, for example as shown in FIG. 15B, the advancement of the platform 5 can stretch the TM 20 as it travels up the ramp 13 without tearing a strip 20a of the TM 20 that is on the ramp 13. For example, the first side 8 and the second side 9 can allow the TM 20 on the ramp 13 (e.g., distal to the first and second lateral blades 10, 11) to remain connected to the TM 20 that is not elevated by the ramp 13. As the TM 20 is elevated, it is under tension that is greater than the tension of the TM 20 when not elevated from the SC 22. Advancement of the ramp 13 facilitates presentation of the TM 20 to the first and second lateral blades 10, 11. According to some embodiments, for example as shown in FIG. 15C, the TM 20 contacts the first and second lateral blades 10, 11 while the TM 20 is elevated (e.g., stretched and/or under tension). In this configuration, the first and second lateral blades 10, 11 incise first and second incisions into the TM 20 to form the strip 20a of the TM 20. The incision is more easily and precisely made due to the elevation of the TM 20. During advancement of the platform 5, at least a portion of the strip 20a can be received within the gap 14 between the first and second lateral blades 10, 11. The strip 20a can have a width W that corresponds to the distance D across the gap 14. The width W can be measured along the X-axis, such as across the first and second incisions and transversely (e.g., orthogonally) to the direction of advancement of the device 12 to form the strip 20a. The distance D can be measured along the X-axis, such as across the first and second lateral blades 10, 11 and transversely (e.g., orthogonally) to the direction of advancement of the device 12 to form the strip 20a. According to some embodiments, for example as shown in FIG. 15D, the strip 20a that has been separated from a remainder of the TM 20 can be removed by a device 30 (e.g., forceps) or by aspiration.

In some cases, bleeding may occur during removal of the TM 20 or during the steps depicted in FIGS. 15B-15C. When this occurs, the surgeon may actuate the fluid transfer mechanism (e.g., press button 136, see FIGS. 1-6) to deliver a dosage of viscoelastic. This may push the blood back into the SC 22 or otherwise move the blood away from the TM 20, allowing the surgeon to continue the procedure without a need for removing the device from the anterior chamber to insert a separate viscoelastic syringe.

The advancement of the platform 5 and the ramp 13 can proceed as the device advances clockwise or counterclockwise. The distal cutting portion is angled so that the dual blades are placed in optimum cutting position. This angle may be such that the cutting tip bends to conform to the area between Schwalbe's line and the scleral spur (SS), an area that encompasses SC. SC is narrow near the cornea and wider near the SS and thus an angled tip is best to present the tissue 20 to the two edges of the TM. The ramp 13 of the cutting tip may be angled so that the tissue 20 is constantly elevated towards the blade as the tip is advanced in circumferential pattern. Between the cutting tip and the first and second lateral blades 10, 11, the ramp 13 is shaped to avoid cutting tissue, such that the TM 20 that is elevated away from the outer wall of the Schlemm's canal 22 remains intact as it advances along the ramp 13. For example, the ramp 13 can include convex or beveled edges that are not sharp enough to cut the TM 20. Endoscopic visualization may also be used to guide the cutting. In some embodiments, the device of the present disclosure may be placed at the end of an endoscope, precluding the need for a gonio lens during treatment. In some embodiments, the device of the present disclosure may be place at the end of an endoscope and the TM may be engaged under direct visualization of the endoscope camera.

A reference to an element in the singular is not intended to mean one and only one unless specifically so stated, but rather one or more. For example, "a" module may refer to one or more modules. An element proceeded by "a," "an," "the," or "said" does not, without further constraints, preclude the existence of additional same elements.

Headings and subheadings, if any, are used for convenience only and do not limit the invention. The word exemplary is used to mean serving as an example or illustration. To the extent that the term include, have, or the like is used, such term is intended to be inclusive in a manner similar to the term comprise as comprise is interpreted when employed as a transitional word in a claim. Relational terms such as first and second and the like may be used to distinguish one entity or action from another without necessarily requiring or implying any actual such relationship or order between such entities or actions.

Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A phrase "at least one of" preceding a series of items, with the terms "and" or "or" to separate any of the items, modifies the list as a whole, rather than each member of the list. The phrase "at least one of" does not require selection of at least one item; rather, the phrase allows a meaning that includes at least one of any one of the items, and/or at least one of any combination of the items, and/or at least one of each of the items. By way of example, each of the phrases "at least one of A, B, and C" or "at least one of A, B, or C" refers to only A, only B, or only C; any combination of A, B, and C; and/or at least one of each of A, B, and C.

It is understood that the specific order or hierarchy of steps, operations, or processes disclosed is an illustration of exemplary approaches. Unless explicitly stated otherwise, or the context clearly dictates otherwise, it is understood that the specific order or hierarchy of steps, operations, or processes may be performed in different order. Some of the steps, operations, or processes may be performed simultaneously. The accompanying method claims, if any, present elements of the various steps, operations or processes in a sample order, and are not meant to be limited to the specific order or hierarchy presented. These may be performed in serial, linearly, in parallel or in different order.

In one aspect, a term coupled or the like may refer to being directly coupled. In another aspect, a term coupled or the like may refer to being indirectly coupled.

Terms such as top, bottom, front, rear, side, horizontal, vertical, and the like refer to an arbitrary frame of reference, rather than to the ordinary gravitational frame of reference. Thus, such a term may extend upwardly, downwardly, diagonally, or horizontally in a gravitational frame of reference.

The disclosure is provided to enable any person skilled in the art to practice the various aspects described herein. In some instances, well-known structures and components are shown in block diagram form in order to avoid obscuring the concepts of the subject technology. The disclosure provides various examples of the subject technology, and the subject technology is not limited to these examples. Various modifications to these aspects will be readily apparent to those skilled in the art, and the principles described herein may be applied to other aspects.

All structural and functional equivalents to the elements of the various aspects described throughout the disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for".

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirements of the applicable patent law, nor should they be interpreted in such a way.

What is claimed is:

1. A medical instrument, comprising:
a housing;
a tool section coupled to the housing;
an interior cavity disposed in the housing;
a piston disposed in the interior cavity;
an interior chamber disposed in the interior cavity;
a button coupled to the piston and disposed on the housing, wherein the button is configured to actuate the piston for pumping fluid through the housing;
a pre-fill chamber;
a sealing member having a first spiral ramp, wherein the sealing member is configured to seal the pre-fill chamber; and
an interface member having a second spiral ramp that slidingly engages with the first spiral ramp, wherein the interface member has a proximal end, a distal end, a connector at the proximal end configured to couple to a fluid source, a projection at the distal end extending through an opening of the sealing member and a fill port on a lateral side of the projection.

2. The medical instrument of claim 1, wherein the housing is an elongate tubular housing having a lateral exterior surface that provides a grip for a human hand, and wherein the button is disposed on a lateral side of the elongate tubular housing.

3. The medical instrument of claim 1, wherein the button comprises a first sloped surface, wherein the piston comprises a second sloped surface, and wherein sliding engagement between the first sloped surface and the second sloped surface is configured to actuate a stroke of the piston.

4. The medical instrument of claim 1, wherein one of the button or the piston comprises a sloped surface, wherein the other of the button or the piston comprises a wheel, and wherein engagement between the sloped surface and the wheel is configured to actuate a stroke of the piston.

5. The medical instrument of claim 1, further comprising: a fluid port coupled to the interior chamber; a first valve disposed at the fluid port; and a second valve disposed on the piston.

6. The medical instrument of claim 1, further comprising: the interior chamber being a first chamber disposed in the interior cavity on a first side of the piston; and a second chamber disposed in the interior cavity on a second side of the piston opposite to the first side of the piston, wherein a forward stroke of the piston causes compression of the first chamber and expansion of the second chamber.

7. The medical instrument of claim 6,
wherein the compression of the first chamber is configured to eject fluid from the first chamber to the tool section, and
wherein the expansion of the second chamber is configured to draw fluid into the second chamber from a fluid source.

8. The medical instrument of claim 1,
wherein the housing is an elongate tubular housing having a distal end and a proximal end;
wherein the tool section is disposed at the distal end of the housing;
wherein a fluid connector is disposed at the proximal end of the housing; and
wherein the interior chamber comprises a fluid exit chamber disposed on a distal side of the piston and the interior cavity further comprises a fluid entry chamber disposed on a proximal side of the piston.

9. The medical instrument of claim 1, further comprising a fluidic channel extending through the piston, wherein the fluidic channel is segmented into a plurality of sub-channels each terminating in a valve.

10. The medical instrument of claim 1,
wherein the tool section comprises an ophthalmic blade at a distal end and a lumen;
wherein the housing is configured to couple to a viscoelastic syringe; and
wherein the piston is configured to transfer viscoelastic fluid from the viscoelastic syringe to the lumen.

11. The medical instrument of claim 10, wherein the ophthalmic blade comprises a dual-blade tip for incising a trabecular meshwork.

12. The medical instrument of claim 1, wherein the tool section is coupled to a first end of the housing and a second end of the housing comprises a luer lock connector configured to attach to a fluid source.

13. The medical instrument of claim 1, further comprising a dose adjustment member coupled to the piston.

14. The medical instrument of claim 13, wherein the dose adjustment member is adjustable to modify a length of travel of the piston and thereby change a volume of a substance delivered upon a forward stroke of the piston.

15. The medical instrument of claim 1, further comprising:
a first check valve disposed at a fluid entry port of the housing;
a second check valve disposed at a fluid exit port of the housing; and
a third check valve disposed on the piston.

16. The medical instrument of claim 1, further comprising:
a lock mechanism configured to lock the piston in a forward position.

17. The medical instrument of claim 1, wherein rotation of the interface member is configured to isolate the fill port from the pre-fill chamber.

* * * * *